(12) United States Patent
Sun et al.

(10) Patent No.: US 10,709,384 B2
(45) Date of Patent: Jul. 14, 2020

(54) WEARABLE HEAT FLUX DEVICES AND METHODS OF USE

(71) Applicant: MC10, Inc., Lexington, MA (US)

(72) Inventors: Hoi-Cheong Steve Sun, Lexington, MA (US); Milan Raj, Natick, MA (US); Xianyan Wang, San Jose, CA (US); Brian Murphy, Medford, MA (US); Valerie Susan Hanson, Medford, MA (US)

(73) Assignee: MC10, INC., Lexington, MA (US)

( * ) Notice: Subject to any disclaimer, the term of this patent is extended or adjusted under 35 U.S.C. 154(b) by 398 days.

(21) Appl. No.: 15/238,488

(22) Filed: Aug. 16, 2016

(65) Prior Publication Data
US 2017/0049397 A1 Feb. 23, 2017

Related U.S. Application Data

(60) Provisional application No. 62/207,145, filed on Aug. 19, 2015.

(51) Int. Cl.
*G01K 3/00* (2006.01)
*A61B 5/00* (2006.01)
(Continued)

(52) U.S. Cl.
CPC .............. *A61B 5/6833* (2013.01); *A61B 5/01* (2013.01); *G01K 1/14* (2013.01); *G01K 7/427* (2013.01); *G01K 13/002* (2013.01); *G01K 17/00* (2013.01)

(58) Field of Classification Search
CPC combination set(s) only.
See application file for complete search history.

(56) References Cited

U.S. PATENT DOCUMENTS

| 3,716,861 A | 2/1973 | Root |
| 3,805,427 A | 4/1974 | Epstein |

(Continued)

FOREIGN PATENT DOCUMENTS

| CN | 202068986 U | 12/2011 |
| DE | 10 2007 046 886 A1 | 4/2009 |

(Continued)

OTHER PUBLICATIONS

U.S. Appl. No. 14/004,408, filed Mar. 9, 2012, R. Ghaffari et al., Integrated Devices to Facilitate Quantitative Assays and Diagnostics.

(Continued)

*Primary Examiner* — Lisa M Caputo
*Assistant Examiner* — Nasir U. Ahmed
(74) *Attorney, Agent, or Firm* — Nixon Peabody LLP

(57) ABSTRACT

Wearable heat flux devices are disclosed that can detect heat flux based on evaporative cooling for determining a core body temperature of a user, and that can heat or cool a surface of a user for reaching a steady-state heat flux to determine the core body temperature of the user. Exemplary heat flux devices can include a heat flux sensor and a wicking layer. The heat flux sensor can be configured to detect heat flux at a location on a user. The wicking layer can be configured to absorb moisture at the location and to transport the moisture above the heat flux sensor. The heat flux subsequently detected by the heat flux sensor includes the evaporative cooling from the evaporation of the moisture.

23 Claims, 10 Drawing Sheets

(51) Int. Cl.
  *G01K 13/00* (2006.01)
  *G01K 1/14* (2006.01)
  *A61B 5/01* (2006.01)
  *G01K 7/42* (2006.01)
  *G01K 17/00* (2006.01)

(56) References Cited

U.S. PATENT DOCUMENTS

| | | | |
|---|---|---|---|
| 3,838,240 A | 9/1974 | Schelhorn | |
| 4,278,474 A | 7/1981 | Blakeslee | |
| 4,304,235 A | 12/1981 | Kaufman | |
| 4,416,288 A | 11/1983 | Freeman | |
| 4,658,153 A | 4/1987 | Brosh | |
| 5,272,375 A | 12/1993 | Belopolsky | |
| 5,306,917 A | 4/1994 | Black | |
| 5,326,521 A | 7/1994 | East | |
| 5,331,966 A | 7/1994 | Bennett | |
| 5,360,987 A | 11/1994 | Shibib | |
| 5,471,982 A | 5/1995 | Edwards | |
| 5,454,270 A | 10/1995 | Brown | |
| 5,491,651 A | 2/1996 | Janic | |
| 5,567,975 A | 10/1996 | Walsh | |
| 5,580,794 A | 12/1996 | Allen | |
| 5,617,870 A | 4/1997 | Hastings | |
| 5,811,790 A | 9/1998 | Endo | |
| 5,817,008 A | 10/1998 | Rafert | |
| 5,907,477 A | 5/1999 | Tuttle | |
| 6,063,046 A | 5/2000 | Allum | |
| 6,265,090 B1 | 7/2001 | Nishide | |
| 6,282,960 B1 | 9/2001 | Samuels | |
| 6,343,514 B1 | 2/2002 | Smith | |
| 6,387,052 B1 | 5/2002 | Quinn | |
| 6,410,971 B1 | 6/2002 | Otey | |
| 6,421,016 B1 | 7/2002 | Phillips | |
| 6,450,026 B1 | 9/2002 | Desarnaud | |
| 6,455,931 B1 | 9/2002 | Hamilton | |
| 6,567,158 B1 | 5/2003 | Falcial | |
| 6,626,940 B2 | 9/2003 | Crowley | |
| 6,628,987 B1 | 9/2003 | Hill | |
| 6,641,860 B1 | 11/2003 | Kaiserman | |
| 6,775,906 B1 | 8/2004 | Silverbrook | |
| 6,784,844 B1 | 8/2004 | Boakes | |
| 6,965,160 B2 | 11/2005 | Cobbley | |
| 6,987,314 B1 | 1/2006 | Yoshida | |
| 6,994,468 B2 * | 2/2006 | Thery | G01J 5/12 136/225 |
| 7,259,030 B2 | 8/2007 | Daniels | |
| 7,265,298 B2 | 9/2007 | Maghribi | |
| 7,302,751 B2 | 12/2007 | Hamburgen | |
| 7,337,012 B2 | 2/2008 | Maghribi | |
| 7,487,587 B2 | 2/2009 | Vanfleteren | |
| 7,491,892 B2 | 2/2009 | Wagner | |
| 7,521,292 B2 | 4/2009 | Rogers | |
| 7,557,367 B2 | 7/2009 | Rogers | |
| 7,618,260 B2 | 11/2009 | Daniel | |
| 7,622,367 B1 | 11/2009 | Nuzzo | |
| 7,727,228 B2 | 6/2010 | Abboud | |
| 7,739,791 B2 | 6/2010 | Brandenburg | |
| 7,759,167 B2 | 7/2010 | Vanfleteren | |
| 7,815,095 B2 | 10/2010 | Fujisawa | |
| 7,960,246 B2 | 6/2011 | Flamand | |
| 7,982,296 B2 | 7/2011 | Nuzzo | |
| 8,097,926 B2 | 1/2012 | De Graff | |
| 8,198,621 B2 | 6/2012 | Rogers | |
| 8,207,473 B2 | 6/2012 | Axisa | |
| 8,217,381 B2 | 7/2012 | Rogers | |
| 8,332,053 B1 | 12/2012 | Patterson | |
| 8,372,726 B2 | 2/2013 | De Graff | |
| 8,389,862 B2 | 3/2013 | Arora | |
| 8,431,828 B2 | 4/2013 | Vanfleteren | |
| 8,440,546 B2 | 5/2013 | Nuzzo | |
| 8,536,667 B2 | 9/2013 | De Graff | |
| 8,552,299 B2 | 10/2013 | Rogers | |
| 8,618,656 B2 | 12/2013 | Oh | |
| 8,664,699 B2 | 3/2014 | Nuzzo | |
| 8,679,888 B2 | 3/2014 | Rogers | |
| 8,729,524 B2 | 5/2014 | Rogers | |
| 8,754,396 B2 | 6/2014 | Rogers | |
| 8,865,489 B2 | 10/2014 | Rogers | |
| 8,886,334 B2 | 11/2014 | Ghaffari | |
| 8,905,772 B2 | 12/2014 | Rogers | |
| 9,012,784 B2 | 4/2015 | Arora | |
| 9,082,025 B2 | 7/2015 | Fastert | |
| 9,105,555 B2 | 8/2015 | Rogers | |
| 9,105,782 B2 | 8/2015 | Rogers | |
| 9,119,533 B2 | 9/2015 | Ghaffari | |
| 9,123,614 B2 | 9/2015 | Graff | |
| 9,159,635 B2 | 10/2015 | Elolampi | |
| 9,168,094 B2 | 10/2015 | Lee | |
| 9,171,794 B2 | 10/2015 | Rafferty | |
| 9,186,060 B2 | 11/2015 | De Graff | |
| 9,226,402 B2 | 12/2015 | Hsu | |
| 9,247,637 B2 | 1/2016 | Hsu | |
| 9,289,132 B2 | 3/2016 | Ghaffari | |
| 9,295,842 B2 | 3/2016 | Ghaffari | |
| 9,324,733 B2 | 4/2016 | Rogers | |
| 9,372,123 B2 | 6/2016 | Li | |
| 9,408,305 B2 | 8/2016 | Hsu | |
| 2001/0012918 A1 | 8/2001 | Swanson | |
| 2001/0021867 A1 | 9/2001 | Kordis | |
| 2002/0000813 A1 | 1/2002 | Hirono | |
| 2002/0026127 A1 | 2/2002 | Balbierz | |
| 2002/0082515 A1 | 6/2002 | Campbell | |
| 2002/0094701 A1 | 7/2002 | Biegelsen | |
| 2002/0113739 A1 | 8/2002 | Howard | |
| 2002/0128700 A1 | 9/2002 | Cross, Jr. | |
| 2002/0145467 A1 | 10/2002 | Minch | |
| 2002/0151934 A1 | 10/2002 | Levine | |
| 2002/0158330 A1 | 10/2002 | Moon | |
| 2002/0173730 A1 * | 11/2002 | Pottgen | A61B 5/01 600/549 |
| 2003/0017848 A1 | 1/2003 | Engstrom | |
| 2003/0045025 A1 | 3/2003 | Coyle | |
| 2003/0097165 A1 | 5/2003 | Krulevitch | |
| 2003/0120271 A1 | 6/2003 | Burnside | |
| 2003/0162507 A1 | 8/2003 | Vatt | |
| 2003/0214408 A1 | 11/2003 | Grajales | |
| 2003/0236455 A1 | 12/2003 | Swanson | |
| 2004/0006264 A1 | 1/2004 | Mojarradi | |
| 2004/0085469 A1 | 5/2004 | Johnson | |
| 2004/0092806 A1 | 5/2004 | Sagon | |
| 2004/0106334 A1 | 6/2004 | Suzuki | |
| 2004/0118831 A1 | 6/2004 | Martin | |
| 2004/0135094 A1 | 7/2004 | Niigaki | |
| 2004/0138558 A1 | 7/2004 | Dunki-Jacobs | |
| 2004/0149921 A1 | 8/2004 | Smyk | |
| 2004/0178466 A1 | 9/2004 | Merrill | |
| 2004/0192082 A1 | 9/2004 | Wagner | |
| 2004/0201134 A1 | 10/2004 | Kawai | |
| 2004/0203486 A1 | 10/2004 | Shepherd | |
| 2004/0221370 A1 | 11/2004 | Hannula | |
| 2004/0243204 A1 | 12/2004 | Maghribi | |
| 2005/0021103 A1 | 1/2005 | DiLorenzo | |
| 2005/0029680 A1 | 2/2005 | Jung | |
| 2005/0067293 A1 | 3/2005 | Naito | |
| 2005/0070778 A1 | 3/2005 | Lackey | |
| 2005/0096513 A1 | 5/2005 | Ozguz | |
| 2005/0113744 A1 | 5/2005 | Donoghue | |
| 2005/0139683 A1 | 6/2005 | Yi | |
| 2005/0171524 A1 | 8/2005 | Stern | |
| 2005/0203366 A1 | 9/2005 | Donoghue | |
| 2005/0248312 A1 | 11/2005 | Cao | |
| 2005/0258050 A1 | 12/2005 | Bruce | |
| 2005/0285262 A1 | 12/2005 | Knapp | |
| 2006/0003709 A1 | 1/2006 | Wood | |
| 2006/0038182 A1 | 2/2006 | Rogers | |
| 2006/0071349 A1 | 4/2006 | Tokushige | |
| 2006/0084394 A1 | 4/2006 | Engstrom | |
| 2006/0106321 A1 | 5/2006 | Lewinsky | |
| 2006/0128346 A1 | 6/2006 | Yasui | |
| 2006/0154398 A1 | 7/2006 | Qing | |
| 2006/0160560 A1 | 7/2006 | Josenhans | |
| 2006/0248946 A1 | 11/2006 | Howell | |
| 2006/0257945 A1 | 11/2006 | Masters | |

(56) References Cited

U.S. PATENT DOCUMENTS

| | | |
|---|---|---|
| 2006/0264767 A1 | 11/2006 | Shennib |
| 2006/0270135 A1 | 11/2006 | Chrysler |
| 2006/0286785 A1 | 12/2006 | Rogers |
| 2007/0027514 A1 | 2/2007 | Gerber |
| 2007/0031283 A1 | 2/2007 | Davis |
| 2007/0108389 A1 | 5/2007 | Makela |
| 2007/0113399 A1 | 5/2007 | Kumar |
| 2007/0123756 A1 | 5/2007 | Kitajima |
| 2007/0190880 A1 | 8/2007 | Dubrow |
| 2007/0270672 A1 | 11/2007 | Hayter |
| 2007/0270674 A1 | 11/2007 | Kane |
| 2008/0036097 A1 | 2/2008 | Ito |
| 2008/0046080 A1 | 2/2008 | Vanden Bulcke |
| 2008/0074383 A1 | 3/2008 | Dean |
| 2008/0096620 A1 | 4/2008 | Lee |
| 2008/0139894 A1 | 6/2008 | Szydlo-Moore |
| 2008/0157235 A1 | 7/2008 | Rogers |
| 2008/0185534 A1 | 8/2008 | Simon |
| 2008/0188912 A1 | 8/2008 | Stone |
| 2008/0193749 A1 | 8/2008 | Thompson |
| 2008/0204021 A1 | 8/2008 | Leussler |
| 2008/0211087 A1 | 9/2008 | Mueller-Hipper |
| 2008/0237840 A1 | 10/2008 | Alcoe |
| 2008/0259576 A1 | 10/2008 | Johnson |
| 2008/0262381 A1 | 10/2008 | Kolen |
| 2008/0287167 A1 | 11/2008 | Caine |
| 2008/0313552 A1 | 12/2008 | Buehler |
| 2009/0000377 A1 | 1/2009 | Shipps |
| 2009/0001550 A1 | 1/2009 | Yonggang |
| 2009/0015560 A1 | 1/2009 | Robinson |
| 2009/0017884 A1 | 1/2009 | Rotschild |
| 2009/0048556 A1 | 2/2009 | Durand |
| 2009/0088750 A1 | 4/2009 | Hushka |
| 2009/0107704 A1 | 4/2009 | Vanfleteren |
| 2009/0154736 A1 | 6/2009 | Lee |
| 2009/0184254 A1 | 7/2009 | Miura |
| 2009/0188017 A1* | 7/2009 | Kruse ............... A41D 31/0027 2/81 |
| 2009/0204168 A1 | 8/2009 | Kallmeyer |
| 2009/0215385 A1 | 8/2009 | Waters |
| 2009/0225751 A1 | 9/2009 | Koenck |
| 2009/0261828 A1 | 10/2009 | Nordmeyer-Massner |
| 2009/0273909 A1 | 11/2009 | Shin |
| 2009/0283891 A1 | 11/2009 | Dekker |
| 2009/0291508 A1 | 11/2009 | Babu |
| 2009/0294803 A1 | 12/2009 | Nuzzo |
| 2009/0322480 A1 | 12/2009 | Benedict |
| 2010/0002402 A1 | 1/2010 | Rogers |
| 2010/0030167 A1 | 2/2010 | Thirstrup |
| 2010/0059863 A1 | 3/2010 | Rogers |
| 2010/0072577 A1 | 3/2010 | Nuzzo |
| 2010/0073669 A1 | 3/2010 | Colvin |
| 2010/0087782 A1 | 4/2010 | Ghaffari |
| 2010/0090781 A1 | 4/2010 | Yamamoto |
| 2010/0090824 A1 | 4/2010 | Rowell |
| 2010/0116526 A1 | 5/2010 | Arora |
| 2010/0117660 A1 | 5/2010 | Douglas |
| 2010/0178722 A1 | 7/2010 | De Graff |
| 2010/0245011 A1 | 9/2010 | Chatzopoulos |
| 2010/0271191 A1 | 10/2010 | De Graff |
| 2010/0298895 A1 | 11/2010 | Ghaffari |
| 2010/0317132 A1 | 12/2010 | Rogers |
| 2010/0321161 A1 | 12/2010 | Isabell |
| 2010/0327387 A1 | 12/2010 | Kasai |
| 2011/0011179 A1 | 1/2011 | Gustafsson |
| 2011/0034912 A1 | 2/2011 | De Graff |
| 2011/0051384 A1 | 3/2011 | Kriechbaum |
| 2011/0054583 A1 | 3/2011 | Litt |
| 2011/0071603 A1 | 3/2011 | Moore |
| 2011/0098583 A1 | 4/2011 | Pandia |
| 2011/0101789 A1 | 5/2011 | Salter |
| 2011/0121822 A1 | 5/2011 | Parsche |
| 2011/0140897 A1 | 6/2011 | Purks |
| 2011/0175735 A1 | 7/2011 | Forster |
| 2011/0184320 A1 | 7/2011 | Shipps |
| 2011/0213559 A1 | 9/2011 | Pollack |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0222375 A1 | 9/2011 | Tsubata |
| 2011/0263950 A1 | 10/2011 | Larson |
| 2011/0277813 A1 | 11/2011 | Rogers |
| 2011/0284268 A1 | 11/2011 | Palaniswamy |
| 2011/0306851 A1 | 12/2011 | Wang |
| 2011/0317737 A1 | 12/2011 | Klewer |
| 2012/0016258 A1 | 1/2012 | Webster |
| 2012/0051005 A1 | 3/2012 | Vanfleteren |
| 2012/0052268 A1 | 3/2012 | Axisa |
| 2012/0065937 A1 | 3/2012 | De Graff |
| 2012/0074546 A1 | 3/2012 | Chong |
| 2012/0087216 A1 | 4/2012 | Keung |
| 2012/0091594 A1 | 4/2012 | Landesberger |
| 2012/0092178 A1 | 4/2012 | Callsen |
| 2012/0092222 A1 | 4/2012 | Kato |
| 2012/0101413 A1 | 4/2012 | Beetel |
| 2012/0101538 A1 | 4/2012 | Ballakur |
| 2012/0108012 A1 | 5/2012 | Yasuda |
| 2012/0126418 A1 | 5/2012 | Feng |
| 2012/0150072 A1 | 6/2012 | Revol-Cavalier |
| 2012/0157804 A1 | 6/2012 | Rogers |
| 2012/0172697 A1 | 7/2012 | Urman |
| 2012/0178367 A1 | 7/2012 | Matsumoto |
| 2012/0226130 A1 | 9/2012 | De Graff |
| 2012/0244848 A1 | 9/2012 | Ghaffari |
| 2012/0256308 A1 | 10/2012 | Helin |
| 2012/0316455 A1 | 12/2012 | Rahman |
| 2012/0327608 A1 | 12/2012 | Rogers |
| 2013/0041235 A1 | 2/2013 | Rogers |
| 2013/0085552 A1 | 4/2013 | Mandel |
| 2013/0099358 A1 | 4/2013 | Elolampi |
| 2013/0100618 A1 | 4/2013 | Rogers |
| 2013/0116520 A1 | 5/2013 | Roham |
| 2013/0118255 A1 | 5/2013 | Callsen |
| 2013/0123587 A1 | 5/2013 | Sarrafzadeh |
| 2013/0135262 A1* | 5/2013 | Alameh ............... G06F 3/0383 345/179 |
| 2013/0150693 A1 | 6/2013 | D'angelo |
| 2013/0185003 A1 | 7/2013 | Carbeck |
| 2013/0192356 A1 | 8/2013 | De Graff |
| 2013/0197319 A1 | 8/2013 | Monty |
| 2013/0200268 A1 | 8/2013 | Rafferty |
| 2013/0211761 A1 | 8/2013 | Brandsma |
| 2013/0214300 A1 | 8/2013 | Lerman |
| 2013/0215467 A1 | 8/2013 | Fein |
| 2013/0225965 A1 | 8/2013 | Ghaffari |
| 2013/0237150 A1 | 9/2013 | Royston |
| 2013/0245388 A1 | 9/2013 | Rafferty |
| 2013/0274562 A1 | 10/2013 | Ghaffari |
| 2013/0313713 A1 | 11/2013 | Arora |
| 2013/0316442 A1 | 11/2013 | Meurville |
| 2013/0316487 A1 | 11/2013 | De Graff |
| 2013/0316645 A1 | 11/2013 | Li |
| 2013/0320503 A1 | 12/2013 | Nuzzo |
| 2013/0321373 A1 | 12/2013 | Yoshizumi |
| 2013/0328219 A1 | 12/2013 | Chau |
| 2013/0331914 A1 | 12/2013 | Lee |
| 2014/0001058 A1 | 1/2014 | Ghaffari |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0140020 A1 | 5/2014 | Rogers |
| 2014/0188426 A1 | 7/2014 | Fastert |
| 2014/0191236 A1 | 7/2014 | Nuzzo |
| 2014/0206976 A1 | 7/2014 | Thompson |
| 2014/0216524 A1 | 8/2014 | Rogers |
| 2014/0240932 A1 | 8/2014 | Hsu |
| 2014/0249520 A1 | 9/2014 | Ghaffari |
| 2014/0303452 A1 | 10/2014 | Ghaffari |
| 2014/0303680 A1 | 10/2014 | Donnelly |
| 2014/0340857 A1 | 11/2014 | Hsu |

(56) References Cited

U.S. PATENT DOCUMENTS

| | | |
|---|---|---|
| 2014/0374872 A1 | 12/2014 | Rogers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0025394 A1 | 1/2015 | Hong |
| 2015/0035680 A1 | 2/2015 | Li |
| 2015/0069617 A1 | 3/2015 | Arora |
| 2015/0099976 A1 | 4/2015 | Ghaffari |
| 2015/0100135 A1 | 4/2015 | Ives |
| 2015/0112165 A1* | 4/2015 | Heikenfeld .......... A61B 5/0531 600/307 |
| 2015/0194817 A1 | 7/2015 | Lee |
| 2015/0237711 A1 | 8/2015 | Rogers |
| 2015/0241288 A1 | 8/2015 | Keen |
| 2015/0260713 A1 | 9/2015 | Ghaffari |
| 2015/0272652 A1 | 10/2015 | Ghaffari |
| 2015/0286913 A1 | 10/2015 | Fastert |
| 2015/0320472 A1 | 11/2015 | Ghaffari |
| 2015/0335254 A1 | 11/2015 | Elolampi |
| 2015/0342036 A1 | 11/2015 | Fastert |
| 2016/0027834 A1 | 1/2016 | de Graff |
| 2016/0045162 A1 | 2/2016 | De Graff |
| 2016/0081192 A1 | 3/2016 | Hsu |
| 2016/0086909 A1 | 3/2016 | Garlock |
| 2016/0095652 A1 | 4/2016 | Lee |
| 2016/0099214 A1 | 4/2016 | Dalal |
| 2016/0099227 A1 | 4/2016 | Dalal |
| 2016/0111353 A1 | 4/2016 | Rafferty |
| 2016/0135740 A1 | 5/2016 | Ghaffari |
| 2016/0178251 A1 | 6/2016 | Johnson |
| 2016/0213262 A1 | 7/2016 | Ghaffari |
| 2016/0213424 A1 | 7/2016 | Ghaffari |
| 2016/0228640 A1 | 8/2016 | Pindado |
| 2016/0232807 A1 | 8/2016 | Ghaffari |
| 2016/0240061 A1 | 8/2016 | Li |
| 2016/0249174 A1 | 8/2016 | Patel |
| 2016/0256070 A1 | 9/2016 | Murphy |
| 2016/0287177 A1 | 10/2016 | Huppert |
| 2016/0293794 A1 | 10/2016 | Nuzzo |
| 2016/0309594 A1 | 10/2016 | Hsu |
| 2016/0322283 A1 | 11/2016 | McMahon |

FOREIGN PATENT DOCUMENTS

| | | |
|---|---|---|
| EP | 0585670 A2 | 3/1994 |
| EP | 0779059 A1 | 6/1997 |
| EP | 1808124 A2 | 7/2007 |
| EP | 2259062 A2 | 12/2010 |
| JP | 05-087511 A | 4/1993 |
| JP | 2005-052212 A | 3/2005 |
| JP | 2009-170173 A | 7/2009 |
| WO | WO 1999/038211 A2 | 7/1999 |
| WO | WO 2005/122285 A2 | 12/2005 |
| WO | WO 2003/021679 A2 | 3/2006 |
| WO | WO 2007/003019 A2 | 1/2007 |
| WO | WO 2007/024983 A2 | 3/2007 |
| WO | WO 2007/116344 A1 | 10/2007 |
| WO | WO 2007/136726 A2 | 11/2007 |
| WO | WO 2008/030960 A2 | 3/2008 |
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/046883 A1 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/124898 A1 | 10/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |
| WO | WO 2015/077559 A1 | 5/2015 |
| WO | WO 2015/080991 A1 | 6/2015 |
| WO | WO 2015/102951 A2 | 7/2015 |
| WO | WO 2015/103483 A1 | 7/2015 |
| WO | WO 2015/103580 A2 | 7/2015 |
| WO | WO 2015/127458 A1 | 8/2015 |
| WO | WO 2015/134588 A1 | 9/2015 |
| WO | WO 2015/138712 A1 | 9/2015 |
| WO | WO2015/145471 A1 | 10/2015 |
| WO | WO 2016/048888 A1 | 3/2016 |
| WO | WO 2016/054512 A1 | 4/2016 |
| WO | WO 2016/057318 A1 | 4/2016 |
| WO | WO 2016/081244 A1 | 5/2016 |
| WO | WO 2016/0127050 A1 | 8/2016 |
| WO | WO 2016/134306 A1 | 8/2016 |
| WO | WO 2016-140961 A1 | 9/2016 |

OTHER PUBLICATIONS

U.S. Appl. No. 13/481,843, filed May 27, 2012, B. Elolampi et al., Electronic, Optical and/or Mechanical Apparatus and Systems and Methods for Fabricating Same.

U.S. Appl. No. 13/499,626, filed Jun. 12, 2012, R. Ghaffari et al., Protective Cases With Integrated Electronics.

U.S. Appl. No. 13/568,022, filed Aug. 6, 2012, R. D'angelo et al., Catheter Balloon Methods and Apparatus Employing Sensing Elements.

U.S. Appl. No. 13/603,290, filed Sep. 4, 2012, C. Rafferty et al., Electronics for Detection of a Condition of Tissue.

U.S. Appl. No. 13/631,739, filed Sep. 28, 2012, C. Rafferty et al., Electronics for Detection of a Property of a Surface.

U.S. Appl. No. 13/646,613, filed Oct. 5, 2012, R. Ghaffari et al., Cardiac Catheter Employing Conformal Electronics for Mapping.

U.S. Appl. No. 13/844,399, filed Mar. 15, 2013, S. Fastert et al., Conformal Electronics Integrated With Apparel.

U.S. Appl. No. 13/844,508, filed Mar. 15, 2013, S. Fastert et al., Monitoring Hit Count for Impact Events.

U.S. Appl. No. 13/844,635, filed Mar. 15, 2013, R. Ghaffari et al., Catheter Balloon Having Stretchable Integrated Circuitry and Sensor Array.

U.S. Appl. No. 13/844,638, filed Mar. 15, 2013, C. Rafferty et al., Embedding Thin Chips in Polymer.

U.S. Appl. No. 13/844,677, filed Mar. 15, 2013, S. Lee et al., Catheter Device Including Flow Sensing.

U.S. Appl. No. 13/844,767, filed Mar. 15, 2013, R. Ghaffari et al., Catheter Balloon Employing Force Sensing Elements.

U.S. Appl. No. 14/276,413, filed May 13, 2014, Y. Hsu et al., Conformal Electronics Including Nested Serpentine Interconnects.

U.S. Appl. No. 14/294,808, filed Jun. 3, 2014, I. Kacyvenski et al., Motion Sensor and Analysis.

U.S. Appl. No. 14/311,686, filed Jun. 23, 2014, J. Fenuccio et al., Band With Conformable Electronics.

(56) References Cited

OTHER PUBLICATIONS

U.S. Appl. No. 14/488,544, filed Sep. 17, 2014, W. Arora et al., Extremely Stretchable Electronics.
U.S. Appl. No. 14/510,868, filed Oct. 9, 2014, B. Ives, Utility Gear Including Conformal Sensors.
U.S. Appl. No. 29/506,439, filed Oct. 15, 2014, X. Li et al., Electronic Device Having Antenna.
U.S. Appl. No. 14/518,856, filed Oct. 20, 2014, R. Ghaffari et al., Systems, Methods, and Devices Using Stretchable or Flexible Electronics for Medical Applications.
U.S. Appl. No. 14/524,817, filed Oct. 27, 2014, X. Li et al., Conformal Electronic Devices.
U.S. Appl. No. 14/588,765, filed Jan. 2, 2015, S. Lee et al., Integrated Devices for Low Power Quantitative Measurements.
U.S. Appl. No. 14/630,335, filed Feb. 24, 2015, B. Keen, Conformal Electronics with Deformation Indicators.
U.S. Appl. No. 14/656,046, filed Mar. 12, 2015, R. Ghaffari et al., Quantification of a Change in Assay.
U.S. Appl. No. 14/726,136, filed May 29, 2015, R. Ghaffari et al., Catheter Balloon Methods and Apparatus Employing Sensing Elements.
U.S. Appl. No. 14/726,142, filed May 29, 2015, R. Ghaffari et al., Cardiac Catheter Employing Conformal Electronics for Mapping.
U.S. Appl. No. 14/746,659, filed Jun. 22, 2015, S. Fastert et al., Conformal Electronics Integrated With Apparel.
U.S. Appl. No. 14/758,946, filed Jul. 1, 2015, S. Fastert et al., Application for Monitoring a Property of a Surface.
U.S. Appl. No. 14/812,197, filed Jul. 29, 2015, B. De Graff et al., Methods and Applications of Non-Planar Imaging Arrays.
U.S. Appl. No. 14/819,040, filed Aug. 5, 2015, B. Elolampi et al., A Method for Fabricating a Flexible Electronic Structure and a Flexible Electronic Structure.
U.S. Appl. No. 14/838,196, filed Aug. 27, 2015, G. Callsen et al., Methods and Apparatus for Conformal Sensing of Force and/or Acceleration at a Person's Head.
U.S. Appl. No. 14/859,112, filed Sep. 18, 2015, C. Rafferty et al., Embedded Thin Chips in Polymer.
U.S. Appl. No. 14/859,680, filed Sep. 21, 2015, D. Garlock, Methods and Apparatuses for Shaping and Looping Bonding Wires That Serve as Stretchable and Bendable Interconnects.
U.S. Appl. No. 14/870,719, filed Sep. 30, 2015, M. Dalal et al., Flexible Electronic Circuits With Embedded Integrated Circuit Die and Methods of Making and Using the Same.
U.S. Appl. No. 14/870,802, filed Sep. 30, 2015, M. Dalal et al., Flexible Interconnects for Modules of Integrated Circuits and Methods of Making and Using the Same.
U.S. Appl. No. 14/874,148, filed Oct. 2, 2015, Stephen P. Lee, Catheter Device Including Flow Sensing.
U.S. Appl. No. 14/924,440, filed Oct. 27, 2015, Bassel De Graff, Systems, Methods, and Devices Having Stretchable Integrated Circuitry for Sensing and Delivering Therapy.
U.S. Appl. No. 15/003,644, filed Jan. 21, 2016, Roozbeh Ghaffari et al., Methods of Detecting Parameters of a Lumen.
U.S. Appl. No. 15/016,937, filed Feb. 5, 2016, Jesus Pindado et al., Method and System for Interacting with an Environment.
U.S. Appl. No. 15/047,314, filed Feb. 18, 2016, Roozbeh Ghaffari et al., Catheter or Guidewire Device Including Flow Sensing and Use Thereof.
U.S. Appl. No. 15/047,333, filed Feb. 18, 2016, Roozbeh Ghaffari et al., Catheter or Guidewire Device Including Flow Sensing and Use Thereof.
U.S. Appl. No. 15/048,576, filed Feb. 19, 2016, Shyamal Patel et al., Automated Detection and Configuration of Wearable Devices Based on-Body Status, Location, and/or Orientation.
U.S. Appl. No. 15/057,762, filed Mar. 1, 2016, Brian Murphy et al., Perspiration Sensor.
U.S. Appl. No. 15/023,556, filed Mar. 21, 2016, Roozbeh Ghaffari, Conformal Sensor Systems for Sensing and Analysis.
U.S. Appl. No. 15/139,256, filed Apr. 26, 2016, Xia Li et al., Flexible Temperature Sensor Including Conformable Electronics.
U.S. Appl. No. 15/038,401, filed May 20, 2016, Huppert et al., Conformal Sensor Systems for Sensing and Analysis of Cardiac Activity.
U.S. Appl. No. 15/160,631, filed May 20, 2016, Lee et al., Ultra-Thin Wearable Sensing Device.
U.S. Appl. No. 15/183,513, filed Jun. 15, 2016, Wang et al., Moisture Wicking Adhesives for Skin-Mounted Devices.
U.S. Appl. No. 15/194,995, filed Jun. 28, 2016, Hsu et al., Strain Isolation Structures for Stretchable Electronics.
U.S. Appl. No. 15/208,444, filed Jul. 12, 2016, McGrane et al., Conductive Stiffener, Method of Making a Conductive Stiffener, and Conductive Adhesive and Encapsulation Layers.
U.S. Appl. No. 15/272,816, filed Sep. 22, 2016, Pindado et al., Method and System for Crowd-Sourced Algorithm Development.
U.S. Appl. No. 15/281,960, filed Sep. 30, 2016, Ghaffari et al., Method and System for Interacting with a Virtual Environment.
U.S. Appl. No. 15/286,129, filed Oct. 5, 2016, Ghaffari et al., Method and System for Neuromodulation and Stimulation.
U.S. Appl. No. 15/337,389, filed Oct. 28, 2016, Arora et al, Extremely Stretchable Electronics.
U.S. Appl. No. 15/108,861, filed Jun. 29, 2016, McMahon et al, Encapsulated Conformal Electronic Systems and Devices, and Methods of Making and Using the Same.
U.S. Appl. No. 12/968,637, filed Dec. 15, 2010, J. Rogers, High-Speed, High-Resolution Electrophysiology In-Vivo Using Conformal Electronics.
U.S. Appl. No. 13/492,636, filed Jun. 8, 2012, J. Rogers, Flexible and Stretchable Electronic Systems for Epidermal Electronics.
U.S. Appl. No. 14/155,010, filed Jan. 14, 2014, R. Nuzzo, Methods and Devices for Fabricating and Assembling Printable Semiconductor Elements.
U.S. Appl. No. 14/479,100, filed Sep. 5, 2014, J. Rogers, Printed Assemblies of Ultrathin, Microscale Inorganic Light Emitting Diodes for Deformable and Semitransparent Displays.
U.S. Appl. No. 14/521,319, filed Oct. 22, 2014, J. Rogers, Stretchable and Foldable Electronic Devices.
U.S. Appl. No. 14/706,733, filed May 7, 2015, J. Rogers, Stretchable and Foldable Electronic Devices.
U.S. Appl. No. 15/084,211, filed Mar. 29, 2016, R. Nuzzo, Methods and Devices for Fabricating and Assembling Printable Semiconductor Elements.
U.S. Appl. No. 15/084,091, filed Mar. 29, 2016, R. Nuzzo, Methods and Devices for Fabricating and Assembling Printable Semiconductor Elements.
U.S. Appl. No. 15/084,112, filed Mar. 29, 2016, J. Rogers, Controlled Buckling Structures in Semiconductor Interconnects and Nanomembranes for Stretchable Electronics.
U.S. Appl. No. 15/217,121, filed Jul. 22, 2016, B. Litt, Flexible and Scalable Sensor Arrays for Recording and Modulating Physiologic Activity.
Carvalhal et al., "Electrochemical Detection in a Paper-Based Separation Device", Analytical Chemistry, vol. 82, No. 3, (1162-1165) (4 pages) (Jan. 7, 2010).
Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).
Ellerbee et al., "Quantifying Colorimetric Assays in Paper-Based Microfluidic Devices by Measuring the Transmission of Light through Paper," Analytical Chemistry, vol. 81, No. 20 8447-8452, (6 pages) (Oct. 15, 2009).
Halsted, "Ligature and Suture Material," Journal of the American Medical Association, vol. LX, No. 15, 1119-1126, (8 pages) (Apr. 12, 1913).
Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).
Kim et al., "Dissolvable Films of Silk Fibroin for Ultrathin Conformal Bio-Integrated Electronics," Nature, 1-8 (8 pages) (Apr. 18, 2010).

(56) References Cited

OTHER PUBLICATIONS

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).
Kim et al., "Stretchable and Foldable Silicon Integrated Circuits," Science, vol. 320, 507-511 (5 pages) (Apr. 25, 2008).
Kim et al., "Electrowetting on Paper for Electronic Paper Display," ACS Applied Materials & Interfaces, vol. 2, No. 11, (3318-3323) (6 pages) (Nov. 24, 2010).
Ko et al., "A Hemispherical Electronic Eye Camera Based on Compressible Silicon Optoelectronics," Nature, vol. 454, 748-753 (6 pages) (Aug. 7, 2008).
Lawrence et al., "Bioactive Silk Protein Biomaterial Systems for Optical Devices," Biomacromolecules, vol. 9, 1214-1220 (7 pages) (Nov. 4, 2008).
Meitl et al., "Transfer Printing by Kinetic Control of Adhesion to an Elastomeric Stamp," Nature, vol. 5, 33-38 (6 pages) (Jan. 2006).
Omenetto et al., "A New Route for Silk," Nature Photonics, vol. 2, 641-643 (3 pages) (Nov. 2008).
Omenetto et al., "New Opportunities for an Ancient Material," Science, vol. 329, 528-531 (5 pages) (Jul. 30, 2010).
Siegel et al., "Foldable Printed Circuit Boards on Paper Substrates," Advanced Functional Materials, vol. 20, No. 1, 28-35, (8 pages) (Jan. 8, 2010).
Tsukada et al., "Structural Changes of Silk Fibroin Membranes Induced by Immersion in Methanol Aqueous Solutions," Journal of Polymer Science, vol. 32, 961-968 (8 pages) (1994).
Wang et al., "Controlled Release From Multilayer Silk Biomaterial Coatings to Modulate Vascular Cell Responses" Biomaterials, 29, 894-903 (10 pages) (Nov. 28, 2008).
Wikipedia, "Ball bonding" article [online]. Cited in PCT/US2015/051210 search report dated Mar. 1, 2016 with the following information "Jun. 15, 2011 [retrieved on Nov. 15, 2015}. Retrieved Dec. 18, 29 from the Internet: <URL: https://web.archive.org/web/20110615221003/hltp://en.wikipedia.org/wiki/Ball_bonding>., entire document, especially para. 1, 4, 5, 6," 2 pages, last page says ("last modified on May 11, 2011").
Bossuyt et al., "Stretchable Electronics Technology for Large Area Applications: Fabrication and Mechanical Characterizations", vol. 3, pp. 229-235 (7 pages) (Feb. 2013).
Jones et al., "Stretchable Interconnects for Elastic Electronic Surfaces". vol. 93, pp. 1459-1467 (9 pages) (Aug. 2005).
Lin et al., "Design and Fabrication of Large-Area, Redundant, Stretchable Interconnect Meshes Using Excimer Laser Photoablation and In Situ Masking", (10 pages) (Aug. 2010).
Kim et al., "A Biaxial Stretchable Interconnect With Liquid-Alloy-Covered Joints on Elastomeric Substrate", vol. 18, pp. 138-146 (9 pages) (Feb. 2009).
Written Opinion and International Search Report of International Application No. PCT/US2016/047205, dated Oct. 27, 2016 (19 pages).

\* cited by examiner

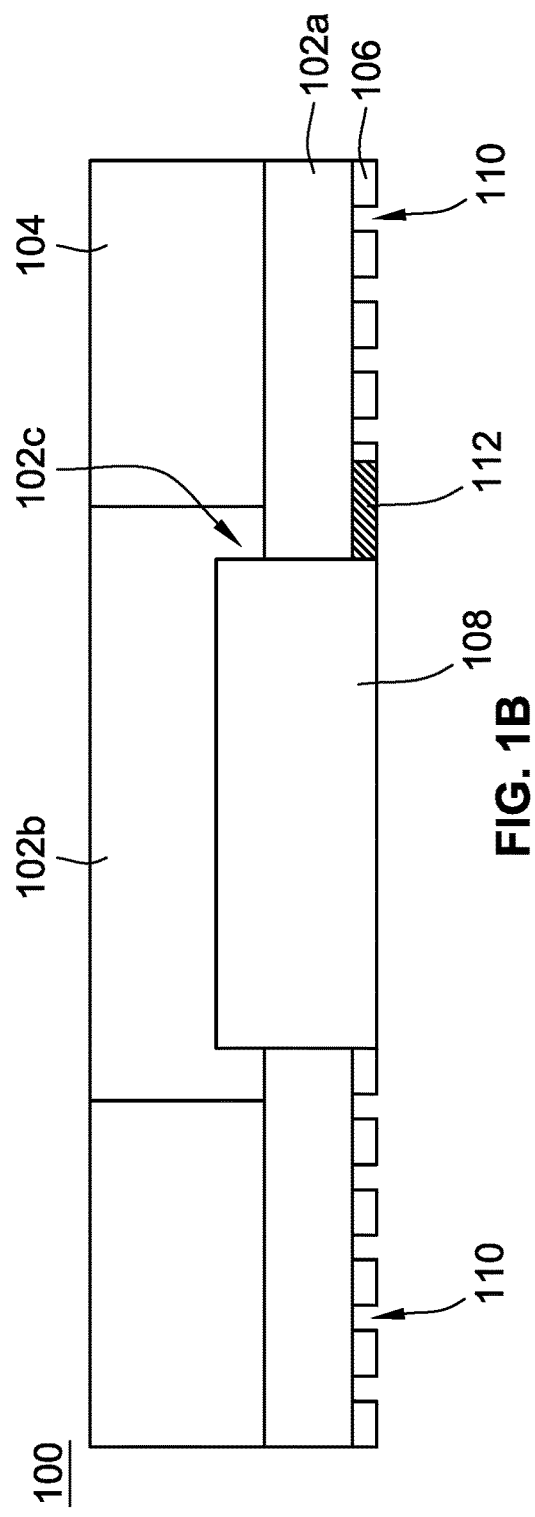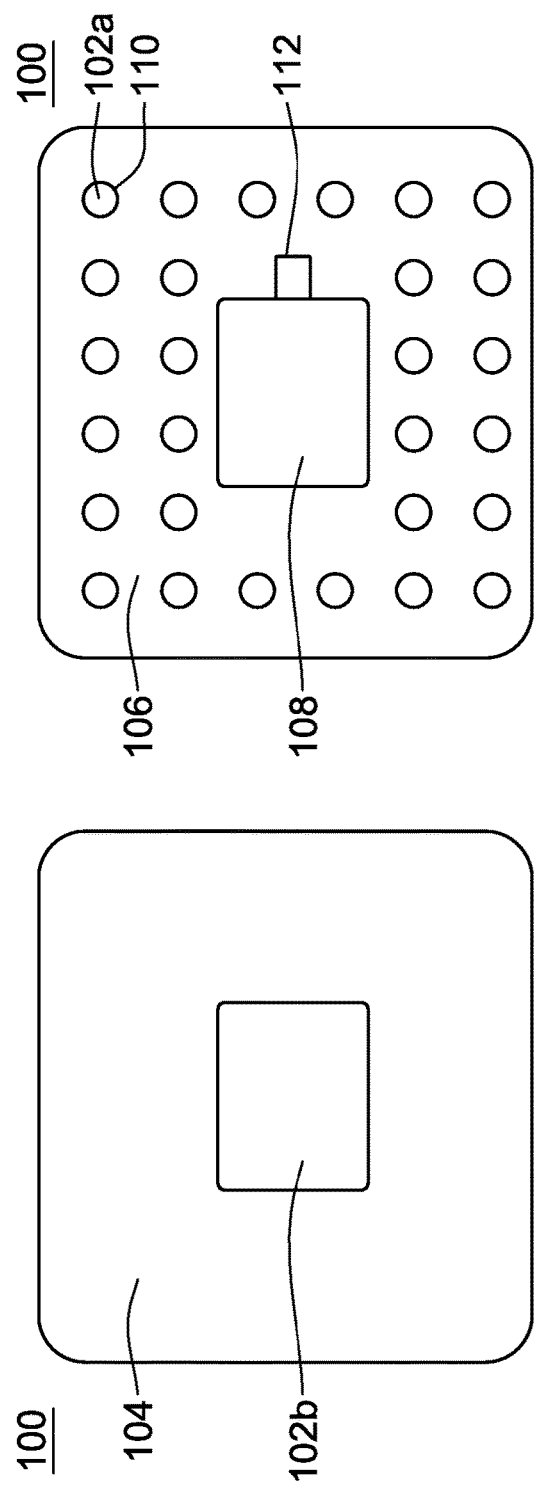
FIG. 1B
FIG. 1C
FIG. 1D

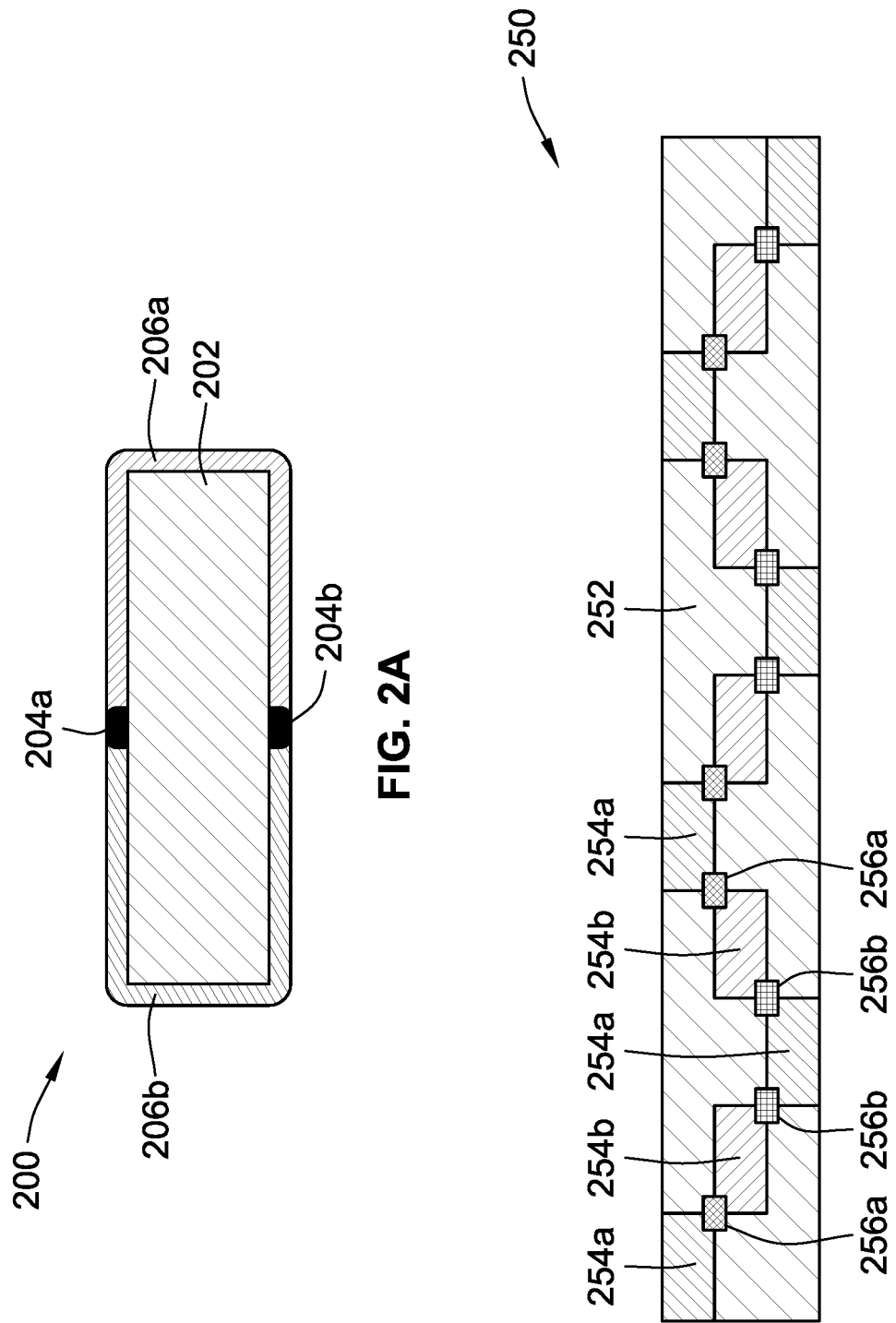

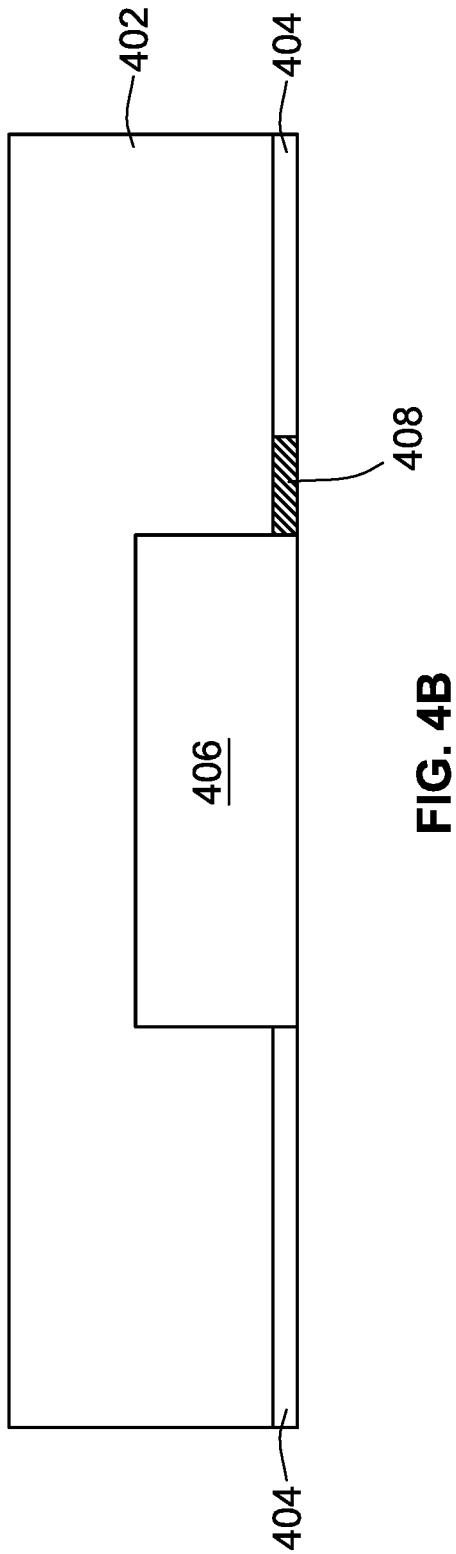
FIG. 4B
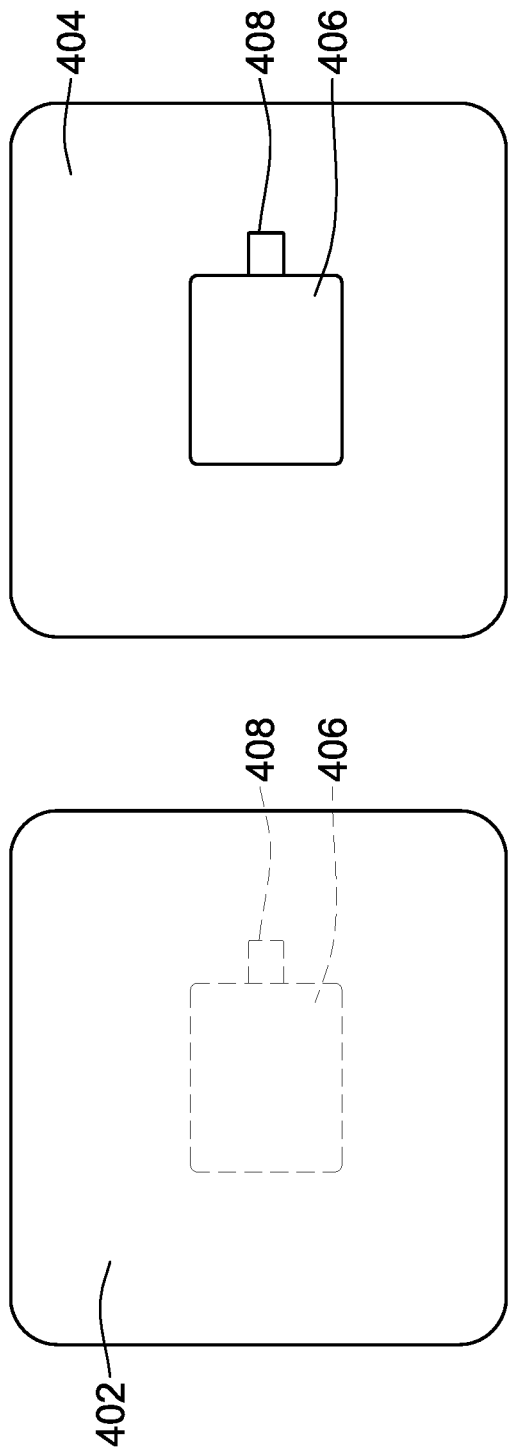
FIG. 4C
FIG. 4D

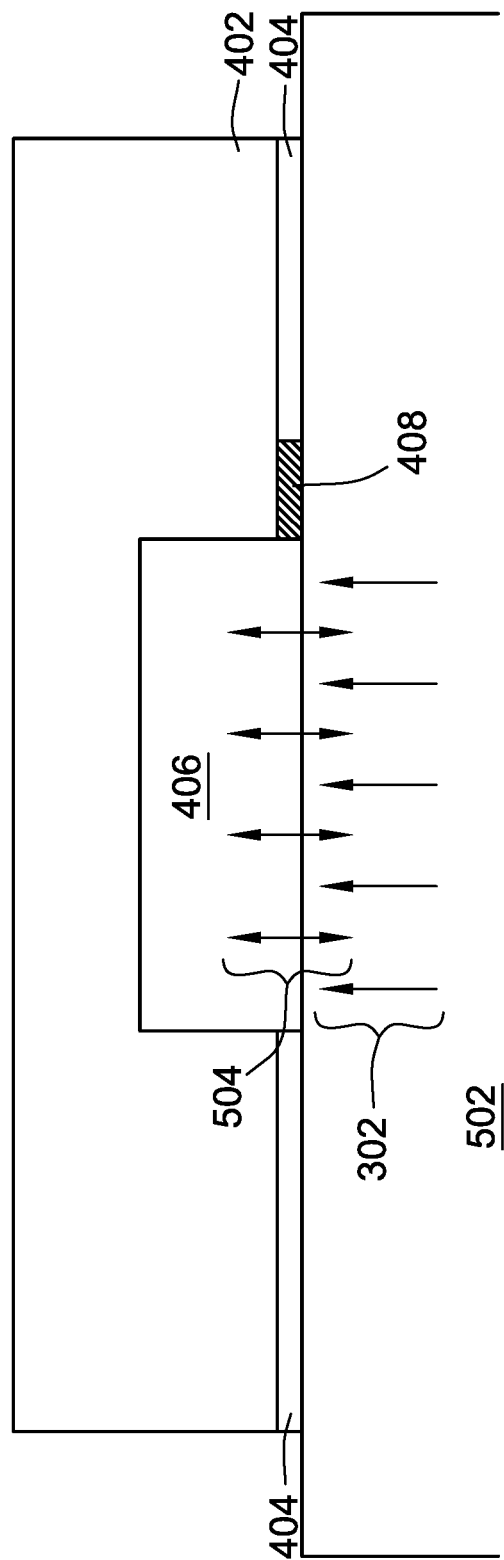

WEARABLE HEAT FLUX DEVICES AND METHODS OF USE

CROSS-REFERENCE TO RELATED APPLICATIONS

The present application claims the benefit of and priority to U.S. Provisional Application No. 62/207,145, filed Aug. 19, 2015, and entitled, "WEARABLE HEAT FLUX DEVICES AND METHODS OF USE," the disclosure of which is hereby incorporated by reference herein in its entirety.

TECHNICAL FIELD

The present disclosure relates generally to sensors. More particularly, aspects of this disclosure relate to sensors wearable on a body, such as a human body.

BACKGROUND

Integrated circuits are the cornerstone of the information age and the foundation of today's information technology industries. The integrated circuit, a.k.a. "IC," "chip," or "microchip," is a set of interconnected electronic components, such as transistors, capacitors, and resistors, which are etched or imprinted onto a semiconducting material, such as silicon or germanium. Integrated circuits take on various forms including, as some non-limiting examples, microprocessors, amplifiers, Flash memories, application specific integrated circuits (ASICs), static random access memories (SRAMs), digital signal processors (DSPs), dynamic random access memories (DRAMs), erasable programmable read only memories (EPROMs), and programmable logic. Integrated circuits are used in innumerable products, including computers (e.g., personal, laptop, and tablet computers), smartphones, flat-screen televisions, medical instruments, telecommunication and networking equipment, airplanes, watercraft, and automobiles.

Advances in integrated circuit technology and microchip manufacturing have led to a steady decrease in chip size and an increase in circuit density and circuit performance. The scale of semiconductor integration has advanced to the point where a single semiconductor chip can hold tens of millions to over a billion devices in a space smaller than a U.S. penny. Moreover, the width of each conducting line in a modern microchip can be made as small as a fraction of a nanometer. The operating speed and overall performance of a semiconductor chip (e.g., clock speed and signal net switching speeds) has concomitantly increased with the level of integration. To keep pace with increases in on-chip circuit switching frequency and circuit density, semiconductor packages currently offer higher pin counts, greater power dissipation, more protection, and higher speeds than packages of just a few years ago.

The advances in integrated circuits have led to related advances within other fields. One such field is sensors. Advances in integrated circuits have allowed sensors to become smaller and more efficient, while simultaneously becoming more capable of performing complex operations. Other advances in the field of sensors and circuitry in general have led to wearable circuitry, a.k.a. "wearable devices" or "wearable systems." Within the medical field, as an example, wearable devices have given rise to new methods of acquiring, analyzing, and diagnosing medical issues with patients, by having the patient wear a sensor that monitors specific characteristics.

One important characteristic of a patient and, indeed, any user in general, is the core body temperature. Deviations from a normal core body temperature present a threat to a patient's health and can indicate potential illnesses. Some current medical procedures also rely on manipulating the core body temperature, such as therapeutic hypothermia, to improve the outcome of, or prevent injury from, certain medical conditions or events. In addition to medical aspects, certain activities that may elevate or lower the core body temperature could benefit from having the ability for real-time, dynamic measurement of the core body temperature. For example, certain professions, such as the military, first responders (e.g., policemen, firemen, and emergency medical technicians), etc., may face conditions that elevate or lower the core body temperature to unsafe conditions. These professions could benefit from being able to dynamically measure the core body temperature to detect unsafe temperature levels within the body.

Certain non-invasive methods have been developed based on wearable devices that measure, among other parameters, the skin temperature at a location of a user to determine the core body temperature. One such technique relies on correlations between the detected heat flux and skin temperature at specific locations of a user to determine the core body temperature. Another technique—specifically referred to as the zero heat flux (ZHF) technique—relies on a wearable device locally insulating a user's skin at a specific location until the temperature of the skin reaches the core body temperature, creating a region of zero heat flow from the body core to the skin.

Although these techniques exist for being able to detect the core body temperature using a wearable device, these techniques suffer from various issues. For example, with respect to the first technique, there currently exists no reliable way for a wearable device to account for the evaporative heat loss from a user sweating during the detection of the heat flux. With respect to the second technique, there currently exists no reliable way to measure the core body temperature in environments where the ambient environmental temperature is greater than the core body temperature.

Accordingly, needs exist for devices and methods for determining the core body temperature using wearable devices that can account for evaporative heat loss in determining the heat flux at a location on a user or that can measure the core body temperature of a subject in environmental conditions that are hotter than the typical core body temperature.

SUMMARY

Aspects of the present invention include a wearable device that determines the heat flux resulting from the transfer for heat from a surface (e.g., tissue, such as skin) of a user. The heat flux can subsequently be used to determine the core body temperature of the user.

Aspects of the present invention include a wearable device that determines the evaporative heat flux resulting from the evaporation of moisture (e.g., sweat) off of a surface (e.g., tissue, such as skin) of a user. The heat flux can subsequently be used to determine the core body temperature of the user.

Aspects of the present invention also include a wearable device that is able to transfer heat toward or away from the surface (e.g., tissue, such as skin) of a user. Using the measured heat flux, the wearable device can determine the core body temperature of the user.

Aspects of the invention include a heat flux device including a heat flux sensor and a wicking layer. The heat flux sensor is configured to detect heat flux at the location of the heat flux device on a user. The wicking layer includes a first portion and a second portion. The first portion surrounds at least part of vertical sides of the heat flux sensor, and the second portion covers a top surface of the heat flux sensor. The wicking layer is configured to absorb moisture from the user at the location through the first portion and to transport the moisture to the second portion for evaporation above the heat flux sensor. The heat flux detected by the heat flux sensor, therefore, includes the heat flux from the evaporation of the moisture Aspects of the invention also include a method of determining evaporative heat flux by a heat flux sensor at a location of a user. The method includes absorbing moisture from the location of the user through a bottom region of a heat flux device placed at the location. The method further includes transporting the moisture to a top region of the heat flux device above the heat flux sensor within the heat flux device. The method further includes determining the heat flux at the location of the user by the heat flux sensor, the heat flux including the evaporative heat flux resulting from evaporation of the moisture at the top region.

Additional aspects of the invention include a heat flux device configured to determine heat flux that includes a determination of evaporative heat flux. The heat flux device including a heat flux sensor configured to detect heat flux at a location on which the heat flux sensor is placed on a user. The heat flux device further includes a wicking layer including a first portion at least partially surrounding the heat flux sensor and a second portion completely covering a top surface of the heat flux sensor. The heat flux device further includes an adhesive layer on a bottom surface of the wicking layer. The adhesive layer is at least partially perforated. The heat flux device further includes a temperature sensor on the bottom surface of the wicking layer, and an insulation layer surrounding the heat flux sensor and the second portion of the wicking layer, and above the first portion of the wicking layer. The bottom surfaces of the heat flux sensor, the adhesive layer, and the temperature sensor are substantially coplanar and form a bottom surface of the heat flux device. An absorption surface area of the second portion of the wicking layer is substantially equal to a surface area of a bottom surface of the heat flux sensor. Based on the foregoing configuration, the heat flux detected by the heat flux sensor includes the evaporative heat flux from the evaporation of moisture adsorbed by the wicking layer that evaporates above the heat flux sensor.

Aspects of the invention also include a method of determining a core body temperature of a user. The method includes detecting heat flux by a heat flex pump placed on a surface (e.g., tissue, such as skin) of the user. The heat flux pump is configured to bi-directionally transfer heat across the surface. The method further includes determining a direction to transfer heat across the surface to bring the heat flux to a steady-state. The method further includes transferring, by operation of the heat flux pump, the heat across the surface according to the determined direction to bring the heat flux to the steady-state. The method further includes determining a temperature at the surface during the steady-state, where the temperature constitutes the core body temperature.

Additional aspects of the invention include a heat flux device wearable on a surface of a user. The heat flux device includes a heat flux pump configured to detect heat flux at the surface and to bi-directionally transfer heat across the surface to bring the heat flux to steady-state. The heat flux device includes a temperature sensor configured to determine a temperature at the surface. The temperature at the surface during the steady-state corresponds to a core body temperature of the user.

The above summary is not intended to represent each embodiment or every aspect of the present disclosure. Rather, the foregoing summary merely provides an exemplification of some of the novel aspects and features set forth herein. The above features and advantages, and other features and advantages of the present disclosure, will be readily apparent from the following detailed description of representative embodiments and modes for carrying out the present invention when taken in connection with the accompanying drawings and the appended claims.

BRIEF DESCRIPTION OF THE DRAWINGS

The disclosure will be better understood from the following description of exemplary embodiments together with reference to the accompanying drawings, in which:

FIG. 1B shows a cross-sectional view of the heat flux device of FIG. 1A along the line 1B-1B, in accord with aspects of the present concepts;

FIG. 1C shows a top view of the heat flux device of FIG. 1A, in accord with aspects of the present concepts;

FIG. 1D shows a bottom view of the heat flux device of FIG. 1A, in accord with aspects of the present concepts;

FIG. 2A shows a cross-sectional view of a heat flux sensor for the heat flux device of FIG. 1A, in accord with aspects of the present concepts;

FIG. 2B shows a cross-sectional view of an alternative heat flux sensor for the heat flux device of FIG. 1A, in accord with additional aspects of the present concepts;

FIG. 4B shows a cross-sectional view of the heat flux device of FIG. 4A along the line 4B-4B, in accord with aspects of the present concepts;

FIG. 4C shows a top view of the heat flux device of FIG. 4A, in accord with aspects of the present concepts;

FIG. 4D shows a bottom view of the heat flux device of FIG. 4A, in accord with aspects of the present concepts;

FIG. 5 shows a cross-sectional view of the heat flux device of FIG. 4A during operation, in accord with aspects of the present concepts;

Figure 1A:
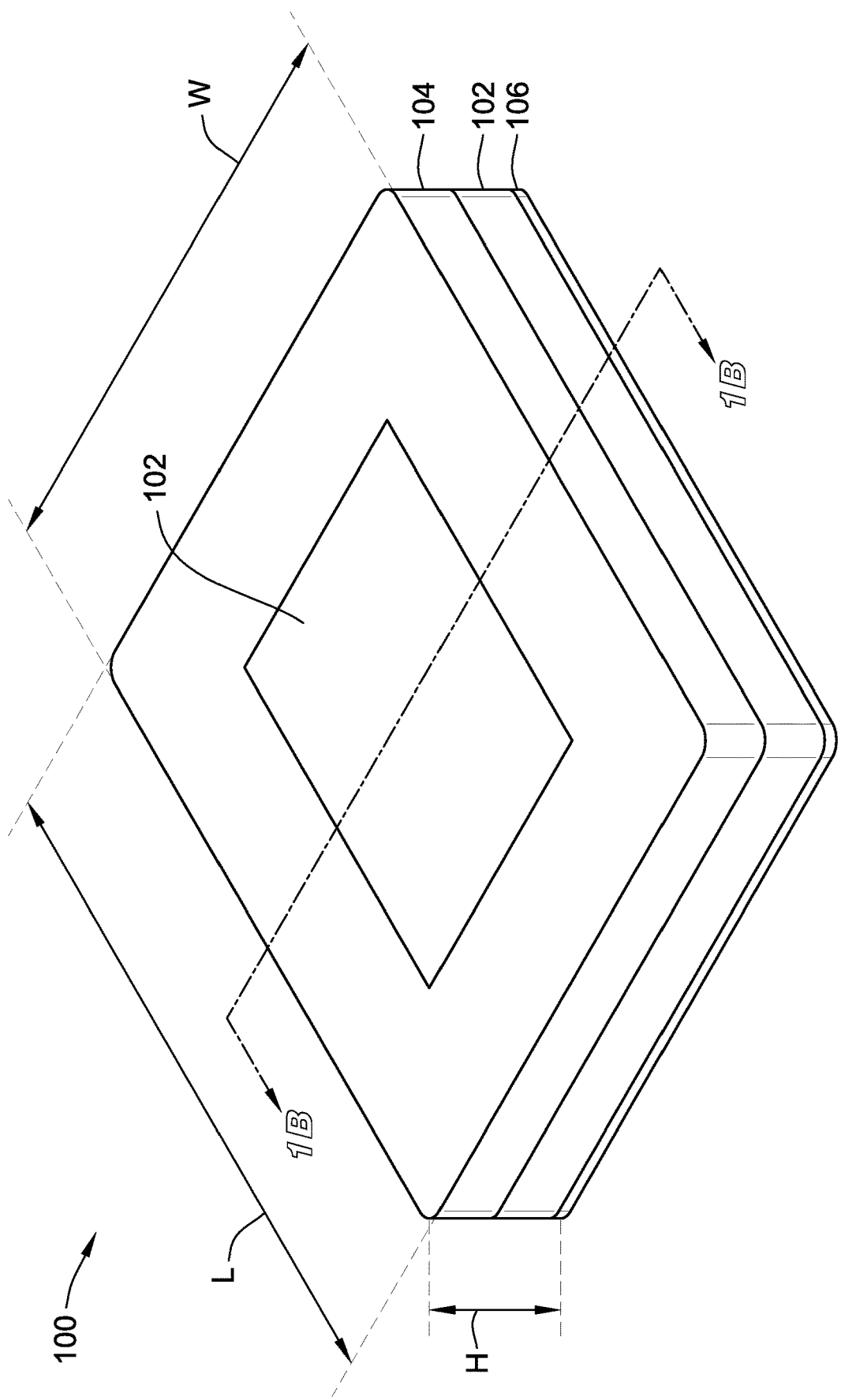
FIG. 1A shows a perspective view of a heat flux device, in accord with aspects of the present concepts.

The present disclosure is susceptible to various modifications and alternative forms, and some representative embodiments have been shown by way of example in the drawings and will be described in detail herein. It should be understood, however, that the invention is not intended to be limited to the particular forms disclosed. Rather, the disclosure is to cover all modifications, equivalents, and alternatives falling within the spirit and scope of the invention as defined by the appended claims.

DETAILED DESCRIPTION OF THE ILLUSTRATED EMBODIMENTS

This disclosure is susceptible of embodiment in many different forms. There are shown in the drawings, and will herein be described in detail, representative embodiments with the understanding that the present disclosure is to be considered as an exemplification of the principles of the present disclosure and is not intended to limit the broad aspects of the disclosure to the embodiments illustrated. To that extent, elements and limitations that are disclosed, for example, in the Abstract, Summary, and Detailed Description sections, but not explicitly set forth in the claims, should not be incorporated into the claims, singly or collectively, by implication, inference, or otherwise. For purposes of the present detailed description, unless specifically disclaimed: the singular includes the plural and vice versa; and the word "including" means "including without limitation." Moreover, words of approximation, such as "about," "almost," "substantially," "approximately," and the like, can be used herein in the sense of "at, near, or nearly at," or "within 3-5% of," or "within acceptable manufacturing tolerances," or any logical combination thereof, for example.

For purposes of illustration and to facilitate an understanding of the invention, the illustrative embodiments are described making reference to "top" and "bottom" and/or "front" and "back" in accordance with how the features are shown in the drawings. These reference designations are provided for convenience and illustration. The inventions can be implemented with the features in other orientations, for example, with the positions reversed and the devices up-side down.

As discussed above, heat flux sensors have been developed for measuring heat flux and determining the core body temperature of a user. Specifically, a ZHF technique relies on locally insulating a location of a user's skin. With the location insulated, the skin temperature at the location gradually elevates to the core body temperature. According to some methods, a heater can be used to elevate the skin temperature rather than relying completely on, for example, an insulation layer to cause the temperature to elevate.

However, existing ZHF devices suffer from several drawbacks. ZHF devices suffer from the inability to use the devices in environmental conditions that are warmer than typical core body temperatures, such as about 37° C. For example, the use of a heater to elevate the skin temperature to near core body temperatures limits the use of ZHF devices to environments that are less than the core body temperature.

Another obstacle for wearable devices that detect heat flux for determining the core body temperature is that such devices do not account for the heat flux resulting from evaporative cooling. The inability for these devices to account for evaporative cooling prevents the devices from accurately determining the heat flux and, therefore, the core body temperature based on the heat flux.

Accordingly, aspects of the present disclosure include wearable heat flux sensing devices that can be used in determining the core body temperature of a user. Such devices can be based on determining the dynamic heat flux from a user, and determining the core body temperature from the heat flux. Specifically, such devices can be used in determining the core body temperature of the user through determining the heat flux at a location of a user, which includes a determination of evaporative cooling from sweating, in combination with the skin temperature at the location, to correlate the heat flux and the skin temperature to the core body temperature.

FIG. 1A shows a perspective view of one example of a heat flux device 100, in accord with aspects of the invention. The heat flux device 100 can be attached to a location on a user, such as attached to the user's skin, and can determine the amount of heat flux leaving or entering the user at the location. Based on the amount of heat flux detected at the location of the heat flux sensor 108, in addition to the skin temperature at the heat flux device 100, the core body temperature $T_c$ of the user can be determined, as explained in detail below.

Although shown generally as a rectangular box, the heat flux device 100 can come in various shapes and sizes. For example, the heat flux device 100 can be circular, triangular, hexagonal, oval, etc. According to some embodiments, the shape of the heat flux device 100 can correspond to a specific location for which the heat flux device 100 is configured to attach to the skin. By way of example, and without limitation, the heat flux device 100 can have a butterfly shape for adhering to the user at a curved or a rounded location, such as around on the user's thigh, forehead, etc. According to some embodiments, the heat flux device 100 is shaped to adhere to preferred locations on the user, such as, for example, the user's sternum, pectoralis, left rib cage, left scapula, and left thigh.

According to some embodiments, the heat flux device 100 is generally flat and is in the form of a patch. According to such a shape, and according to some embodiments, the heat flux device 100 has a length L of 2 to 6 millimeters (mm), such as 4 mm, a width W of 2 to 6 mm, such as 4 mm, and a height H of 0.025 to 2 mm, such as 0.3 mm. Accordingly, the dimensions allow for a small and unobtrusive overall profile for the heat flux device 100. However, the heat flux device 100 can have dimensions other than the specific dimensions provided herein without departing from the spirit and scope of the present disclosure. Based on these dimensions and shape, the heat flux device 100 is formed to have a low thermal mass.

As shown in FIG. 1A, the heat flux device 100 includes a wicking layer 102, an insulation layer 104, and an adhesive layer 106. The wicking layer 102 absorbs fluid, such as sweat, from the bottom surface or region of the wicking layer 102 and transports the fluid to the top surface or region of the wicking layer 102.

The insulation layer 104 is above a portion of the wicking layer 102 and surrounds a portion of the wicking layer 102. The insulation layer 104 insulates the heat flux device 100 and aids in directing fluid to the top surface or region of the wicking layer 102 by acting as a barrier for the fluid. The insulation layer 104 can be formed of one or more insulation materials, such as, for example, thermoplastics, engineering plastics, and foamy plastics. Specific examples of the insulation materials include, for example, neoprene, high-density polyethylene (HDPE), ultra-high-molecular-weight polyethylene (UMWPE), TEFLON®, polyether ether ketone (PEEK), polyimide, and polyurethane. The adhesive layer 106 attaches the heat flux device to the user, such as to the user's skin, and is discussed in greater detail below.

Referring to FIG. 1B, FIG. 1B shows a cross-sectional view of the heat flux device 100 along the line 1B-1B in FIG. 1A, in accord with aspects of the invention. At a general center of the heat flux device 100 is a heat flux sensor 108. However, the heat flux sensor 108 can be located other than at the center of the heat flux device 100, such as closer to one side or corner of the heat flux device 100. The heat flux sensor 108 can be various different types of heat flux sensors, as discussed in greater detail below. The heat flux device 100 is designed so that the heat flux sensor 108 is in direct contact with the user, such as the user's skin, to facilitate heat transfer between the user and the heat flux sensor 108.

Although described above generally as a wicking layer 102 (e.g., in the singular), according to some embodiments, the wicking layer 102 includes two distinct portions. Specifically, the wicking layer 102 includes portion 102a and portion 102b. As shown, portion 102a surrounds at least part of the vertical sides of the heat flux sensor 108 and is below the insulation layer 104. Portion 102b covers the top surface of the heat flux sensor 108 and is surrounded by the insulation layer 104. As will be described in greater detail with respect to FIG. 3, moisture (e.g., sweat) is initially absorbed from the skin once the moisture is secreted from the skin. Specifically, the moisture is collected through absorption by portion 102a of the wicking layer 102. Based on the natural capillary action within portion 102a of the wicking layer 102, the moisture is transported upwards towards portion 102b of the wicking layer 102. Once within portion 102b of the wicking layer 102, the moisture evaporates above the heat flux sensor 108.

The wicking layer 102 also includes an overlap area 102c where portions 102a and 102b overlap. The overlap area 102c transports the moisture absorbed by portion 102a of the wicking layer 102 to portion 102b of the wicking layer 102 based on a capillary action. The material that forms the overlap area 102c can be the same material or a different material than the material(s) that form portions 102a and 102b of the wicking layer 102. With the overlap area 102c formed of a different material, the different material can have a different thermal conductivity than the material(s) that form portions 102a and 102b. The thermal mismatch between the different conductivities disrupts heat flow.

According to some embodiments, the entire wicking layer 102 can be formed of a single material. Alternatively, the wicking layer 102 can be formed of more than one material. By way of example, and without limitation, portions 102a and 102b of the wicking layer 102 can be formed of two different materials. According to some embodiments, portion 102a is formed of a moisture-absorbing material, such as a sweat-absorbing material. Accordingly, portion 102a absorbs sweat from a bottom surface of portion 102a of the wicking layer 102 and transports the sweat to the top of portion 102a of the wicking layer 102. By way of example, and without limitation, portion 102a can be formed of microfiber clothes, cellulose, hydrophilic polyurethane foam, hydrogels, etc.

According to some embodiments, portion 102b is formed of a skin-simulating material. The skin-simulating material forming portion 102b is configured to absorb the moisture from portion 102a and allow the moisture to evaporate above the heat flux sensor 108, similar to the skin of a user. Moreover, the skin-simulating material of portion 102b is configured to mimic the properties of the user's skin, such as the heat and/or moisture transport properties of the user's skin so that the evaporation of the moisture within the skin-simulating material accurately mimics the evaporation of swear on a user's skin. According to some embodiments, the skin-simulating material is porous to allow for the transport of the fluid through the material and to simulate the porous nature of human skin. By way of example, and without limitation, the skin-simulating material can be, for example, hydrogels, animal skins, hydrocolloids, etc. To mimic the thermal properties of human skin, the thermal conductivity of the skin-simulating material is selected to be 0.3 to 0.5 W/mK. By way of a specific example, KAPTON® MT can be used as the skin-simulating material.

The heat flux device 100 further includes an adhesive layer 106. The adhesive layer 106 attaches the heat flux device 100 to the user, such as to the user's skin. The adhesive layer 106 is formed of a biocompatible adhesive. According to some embodiments, the adhesive layer 106 is formed of a moisture-permeable adhesive, such as, for example, hydrogels, hydrocolloids, etc. Alternatively, according to some embodiments, the adhesive layer 106 is formed of a moisture-impermeable adhesive, such as, for example, acrylics and silicone gels.

For an adhesive layer 106 formed of a moisture-impermeable adhesive, the adhesive layer further includes perforations 110 to allow moisture (e.g., water, sweat, etc.) to pass through the adhesive layer 106 and contact the bottom surface of the wicking layer 102 (e.g., bottom surface of portion 102a of the wicking layer 102). Alternatively, the adhesive layer 106 formed of a moisture-permeable adhesive can also include perforations 110 to further allow water to pass through the adhesive layer 106 and contact the bottom surface of the wicking layer 102 (e.g., bottom surface of portion 102a of the wicking layer 102).

Because sweat is absorbed and passes through the wicking layer 102, the area of the bottom surface of the wicking layer 102 is formed to be substantially the same area (e.g., within a 5%, a 2%, a 1%, or a negligible difference) as the bottom surface of the heat flux sensor 108. Because the bottom surfaces of the wicking layer 102 and the heat flux sensor 108 have the same area, the wicking layer 102 absorbs an amount of sweat that would otherwise evaporate on the area of the skin below the heat flux sensor 108 to accurately represent the heat flux generated by evaporation corresponding to the location of the heat flux sensor 108.

According to some embodiments, the surface area of the adhesive layer 106 also matches the area of the heat flux sensor 108 (e.g., within a 5%, a 2%, a 1%, or a negligible difference) and the wicking layer 102 so that the sweat collected from the adhesive layer 106 matches the area under the heat flux sensor 108. Alternatively, the adhesive layer 106 does not have the same dimensions (e.g., length and width) as the wicking layer 102. Rather, the adhesive layer 106 can be smaller than the wicking layer 102. Having a smaller adhesive layer 106 presents a larger area of the wicking layer 102 that is exposed to the user's skin, rather than the adhesive layer 106 being between the skin of the user and the wicking layer 102 across the entire bottom surface of the heat flux device 100. The surface area of the adhesive layer 106 can be smaller than the surface area of the wicking layer 102 depending on the ability of the adhesive layer 106 to maintain the heat flux device 100 attached to the skin of the user.

According to some embodiments, the heat flux sensor 108 is encapsulated to protect the heat flux sensor 108 from corrosion, such as sweat-induced corrosion. Moreover, the material used to encapsulate the heat flux sensor 108 can have a low thermal resistivity that allows the heat flux sensor 108 to detect changes in temperature despite being encapsulated. Further, other portions of the heat flux device 100 can be formed of materials that are resistant to corrosion, such as the insulation layer 104, to not require that the other portions are encapsulated. Alternatively, the other portions of the heat flux device 100 also can be encapsulated to protect the heat flux device 100 from corrosion.

According to some embodiments, the heat flux device 100 further includes a temperature sensor 112. The bottom surface of the temperature sensor 112 is coplanar with the bottom surface of the heat flux sensor 108 so that the temperature sensor 112 contacts the user's skin and detects the temperature of the skin. As shown in FIG. 1B, the bottom surfaces of the adhesive layer 106, the heat flux sensor 108, and the temperature sensor 112 form a planar interface with the user's skin when the heat flux device 100 is on a level surface. As described herein, although the heat flux device 100 can bend and/or flex, such as when attached to a user, the adhesive layer 106, the heat flux sensor 108, and the temperature sensor 112 effectively remain coplanar (e.g., a curved plane) and present a single continuous interface between the heat flux device 100 and the user's skin.

FIGS. 1C and 1D show a top view and a bottom view, respectively, of the heat flux device 100, in accord with aspects of the invention. As shown in FIG. 1C, the top surface of the heat flux device 100 includes the top surface of the insulation layer 104 that surrounds the top surface of the wicking layer 102, particularly the top surface of portion 102b of the wicking layer 102. As shown in FIG. 1D, the bottom surface of the heat flux device 100 includes the bottom surface of the adhesive layer 106, which includes the perforations 110, surrounding the bottom surface of the heat flux sensor 108. The perforations 110 reveal the wicking layer 102 below the adhesive layer 106, particularly portion 102a of the wicking layer 102. Also, on the bottom surface of the heat flux device 100 is the temperature sensor 112.

As discussed above, the heat flux sensor 108 can be one of various different types of heat flux sensors and have one of various different types of configurations. According to some embodiments, the configuration of the heat flux sensor 108 can be based on the Seebeck effect or the Peltier effect. According to the heat flux sensor 108 being based on the Seebeck effect, the overall power requirements of the heat flux sensor 108 and the heat flux device 100 can be very low based on the power required to operate the heat flux sensor 108 being based on a temperature differential experienced above the user's skin.

Referring to FIG. 2A, FIG. 2A shows a cross-sectional view of an exemplary heat flux sensor 200 that can be used in the heat flux device 100 (e.g., as the heat flux sensor 108), in accord with aspects of the present disclosure. The heat flux sensor 200 includes a thermal resistance layer 202, which is a material with a known thermal resistivity k. The thermal resistance layer 202 can be formed of various different materials of a known thermal resistivity k. To reduce the thermal mass of the heat flux device 100, the material selected for the thermal resistance layer 202 is chosen to have a low thermal mass.

According to some embodiments, and to detect the temperature differential across the thermal resistance layer 202, the heat flux sensor 200 further includes thermocouple junctions 204a and 204b on opposite sides of the thermal resistance layer 202 and formed as junctions between two dissimilar conductors, such as two dissimilar metals. By way of example, the junctions 204a and 204b are formed based on the junctions of two dissimilar metal wires 206a and 206b. By way of example, and without limitation, the two metal wires 206a and 206b can be formed of chromel and constantan, iron and constantan, chromel and alumel, nicrosil and nisil, copper and constantan, among others. Based on the thermocouple junctions 204a and 204b being on opposite surfaces of the thermal resistance layer 202, the thermocouple junctions 204a and 204b experience a temperature gradient based on different temperatures being on the opposite sides of the thermal resistance layer 202. By way of example, and without limitation, thermocouple junction 204a corresponds to an ambient air side of the heat flux sensor 200, and thermocouple junction 204b corresponds to a skin side of the heat flux sensor 200, with the heat flux sensor 200 positioned within the heat flux device 100 (e.g., as the heat flux sensor 108) and the heat flux device 100 attached to the user.

Based on the Seebeck effect, with the heat flux sensor 200 within the heat flux device 100 as the heat flux sensor 108, the heat flux sensor 200 measures the heat flux Q between the user's skin and the ambient environment according to the equation:

$$Q = k(T_1 - T_2) \quad (1)$$

where k is the thermal resistivity of the thermal resistance layer 202, $T_1$ is the temperature experienced at the thermocouple junction 204a, and $T_2$ is the temperature experienced at the thermocouple junction 204b.

Based on the Seebeck effect, the voltage output V of the heat flux sensor 200 is based on the equation:

$$V = S(T_1 - T_2) \quad (2)$$

where S is the Seebeck coefficient, $T_1$ is the temperature at the thermocouple junction 204a, and $T_2$ is the temperature at the thermocouple junction 204b. Comparing Equations 1 and 2, the voltage output V based on the Seebeck effect is related to the heat flux Q according to:

$$V = Q(S/k) \quad (3)$$

or $$V = Q \cdot k' \quad (4)$$

where k' is S/k. Based on Equations 1-4, the voltage output V based on the Seebeck effect is related to the heat flux Q based on the temperature difference experienced between the thermocouple junctions 204a and 204b. Accordingly, measuring the voltage output V based on the configuration of the heat flux sensor 200 provides a measurement of the heat flux Q above the user's skin. As described in detail below, determining the heat flux Q allows for determining the core body temperature of the user.

FIG. 2B shows a cross-sectional view of another exemplary heat flux sensor 250 that can be used in the heat flux device 100 (e.g., as heat flux sensor 108), in accord with additional aspects of the invention. The heat flux sensor 250 includes a thermal resistance layer 252. Similar to the thermal resistance layer 202, the thermal resistance layer 252 is a material with a known thermal resistivity k. The thermal resistance layer 252 can be formed of the same material or a different material than the thermal resistance layer 202.

The heat flux sensor 250 is formed of multiple thermocouples arranged in series, also referred to as a thermopile. However, according to some embodiments, the multiple thermocouples may alternatively be arranged in parallel. As shown in FIG. 2B, the heat flux sensor 250 includes positive thermocouple metals 254a and negative thermocouple metals 254b. The positive thermocouple metals 254a and the negative thermocouple metals 254b can be n-type conductors and p-type conductors, or vice versa. The positive thermocouple metals 254a and the negative thermocouple metals 254b meet at upper thermocouple junctions 256a and lower thermocouple junctions 256b.

According to the configuration of the heat flux sensor 250, the heat flux Q is measured according to Equations 1-4 discussed above, with the output voltage generated being a function of the number of junctions within the heat flux sensor 205.

Although discussed above as two specific examples of the heat flux sensor 108 of the heat flux device 100, aspects of the heat flux sensor 108 can vary without departing from the spirit and scope of the present disclosure. By way of example, and without limitation, the heat flux sensor 108 can include other components, or various numbers of thermocouples arranged in series or in parallel on both sides of a thermal resistance layer, to detect the heat flux at the location of the user's skin. The above described approaches with respect to the heat flux sensors 200 and 250 are merely to provide exemplary embodiments and are not meant to be limiting.

Although not shown in FIGS. 2A and 2B, the heat flux sensors 200 and 250 and, indeed, any heat flux sensor 108 in general, includes one or more outputs to connect the heat flux sensors 200 and 250 to an external device that processes, stores, and/or displays the heat flux measurements provided by the heat flux sensors. By way of example, and without limitation, according to some embodiments, the heat flux sensor 108 can include outputs that allow the heat flux sensor 108 to provide real time measurements to a controller (e.g., processor) that uses the heat flux measurements in one or more processes for determining the core body temperature of the user. Alternatively, or in addition, the outputs provide real time heat flux measurements to a display that displays the heat flux measurements, or to a storage device that stores the heat flux measurements on an external device to be displayed and/or analyzed at a later time. Alternatively, the heat flux device 100 can include one or more storage components and/or one or more controllers (e.g., processors) that allow the heat flux device 100 to store the heat flux measurements and/or process the heat flux measurements directly, rather than transferring the heat flux measurements to another device or component. By way of example, and without limitation, the one or more storage components can include flash memory, SRAMs, DRAMs, and the like. In the case of the heat flux measurements being stored on the one or more storage components, the heat flux measurements can be transferred later by one or more wired or wireless communication components to an external device for subsequent display and/or analysis.

Figure 3:
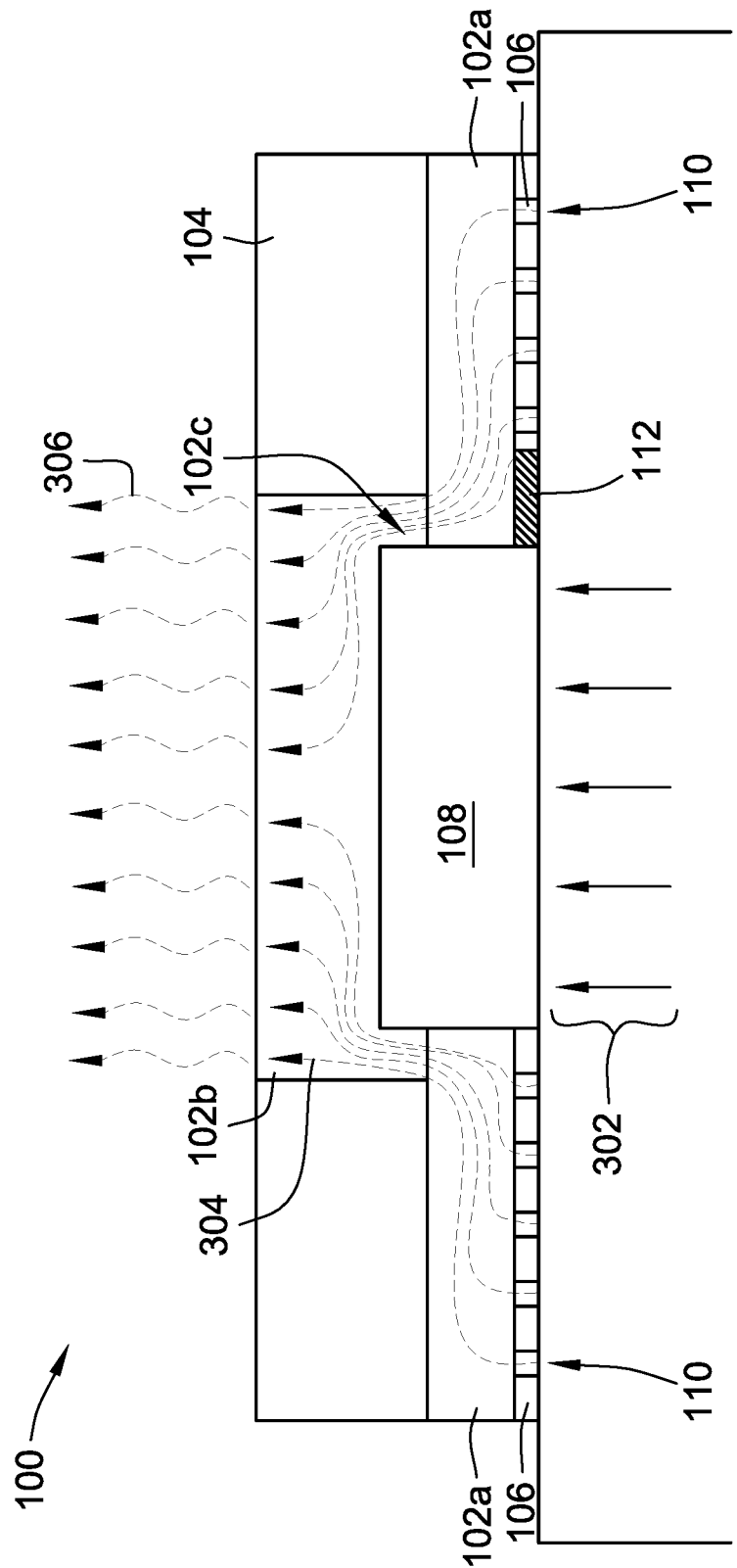
FIG. 3 shows a cross-sectional view of the heat flux device of FIG. 1A during operation, in accord with aspects of the present concepts.

Referring to FIG. 3, FIG. 3 shows operation of the heat flux device 100 attached to the skin 300 of a user, in accord with aspects of the invention. With the heat flux device 100 attached to the skin 300 of a user, the heat flux device 100, through the heat flux sensor 108, measures the heat flux at the location of the heat flux device 100. Specifically, arrows 302 generally represent the heat flux from the user generated by the user and transferred to the heat flux sensor 108 based on conduction, convention, and/or radiation.

Further, as the user sweats, the sweat below the heat flux device 100 is absorbed by the wicking layer 102, specifically portion 102a of the wicking layer, through the perforations 110 in the adhesive layer 106, as shown by arrows 304. The sweat 304 is initially absorbed within portion 102a of the wicking layer 102. From there, the capillary action of portion 102a of the wicking layer 102 transports the sweat 304 to portion 102b of the wicking layer 102, through the overlap area 102c. Once in portion 102b of the wicking layer 102, the sweat evaporates, as shown by arrows 306. Evaporation of the sweat 304 cools the heat flux device 100 based on evaporative cooling and, accordingly, the heat flux sensor 108 within the heat flux device 100 registers the evaporative cooling as part of the measured heat flux. Because the sweat is emitted from the skin below the adhesive layer 106, the evaporative energy comes from the skin and is registered by the heat flux sensor 108 within the heat flux device 100. Thus, the routing the sweat 304 by the wicking layer 102 within the heat flux device 100 allows the heat flux device 100 to measure the heat flux caused by the evaporative cooling of the sweat, in addition to the heat flux based on conduction, convection, and radiation. Accordingly, the heat flux device 100 determines the total thermal energy during sweating and the associated evaporative cooling, rather than only the heat loss (or gain) by conduction, convection, and radiation.

Once the heat flux is determined at a location on a user, in addition to the skin temperature at the location by the temperature sensor 112, the core body temperature can be calculated. Specifically, algorithms can be pre-derived that correlate the detected heat flux at a location, which determines evaporative cooling as discussed above, to the skin temperature at the same location. By way of example, and without limitation, known core body temperatures detected through other techniques, such as invasive techniques (e.g., rectal or esophageal probes, ingested telemetry pills, etc.), are correlated to specific locations of the heat flux device 100, along with the measured heat flux and skin temperature for the specific locations. Using multiple linear regressions, for example, algorithms are derived that determine core body temperature as a function of the measured heat flux, which can be determined as function of evaporative cooling, and the skin temperature. The derived algorithms can be general for all locations on the body, or can be specific to one or more locations. By way of example, and without limitation, an algorithm can be derived that is specific to a location on the body, such as the forehead. With the heat flux device 100 placed on the forehead, the determined heat flux and skin temperature can be entered into the algorithm to determine the core body temperature. Moreover, because the heat flux determined by the heat flux device 100 includes the evaporative cooling caused by, for example, sweating, the derived algorithms and locations of the heat flux device 100 can be for locations on a user that were previously unreliable because of sweating, such as the forehead, among other locations.

According to some embodiments, the heat flux device 100 further can be configured as a sweat rate sensor by extracting the sweat vaporization rate from the heat flux Q. By way of example, and without limitation, parameters, such as measurements of the skin temperature, the heat flux Q, and the location of the heat flux device 100, can be used in an algorithm to determine the sweat vaporization rate.

The heat flux sensors 200 and 250 are examples of the heat flux sensor 108 within the heat flux device 100 that are based on the Seebeck effect. Alternatively, according to some embodiments, the heat flux sensor 108 can be configured based on the Peltier effect, such as a Peltier cooler, by providing a current source connected to or within the heat flux device 100. In such a configuration, the heat flux sensor 108 can both detect heat flux and generate heat flux (e.g., pump heat) across the surface of the user's skin, such as in to the user or out of the user.

The ability to determine evaporative heat loss is one obstacle in determining the core body temperature of a user, according to one type of wearable device; specifically, a wearable device that detects the core body temperature based on the dynamic heat flux at a location of the user in combination with the skin temperature. As discussed above, another approach for detecting the core body temperature of a user is according to the ZHF technique, which relies on locally insulating the skin and elevating the skin temperature to approximately the core body temperature. However, existing ZHF devices use a heater to elevate the skin temperature to near the core body temperature, which limits the use of existing ZHF devices to environments that are cooler than the typical core body temperature of a user (e.g., 37° C.). However, aspects of the present disclosure overcome these obstacles according to the following disclosed alternative wearable heat flux device 400.

Figure 4A:
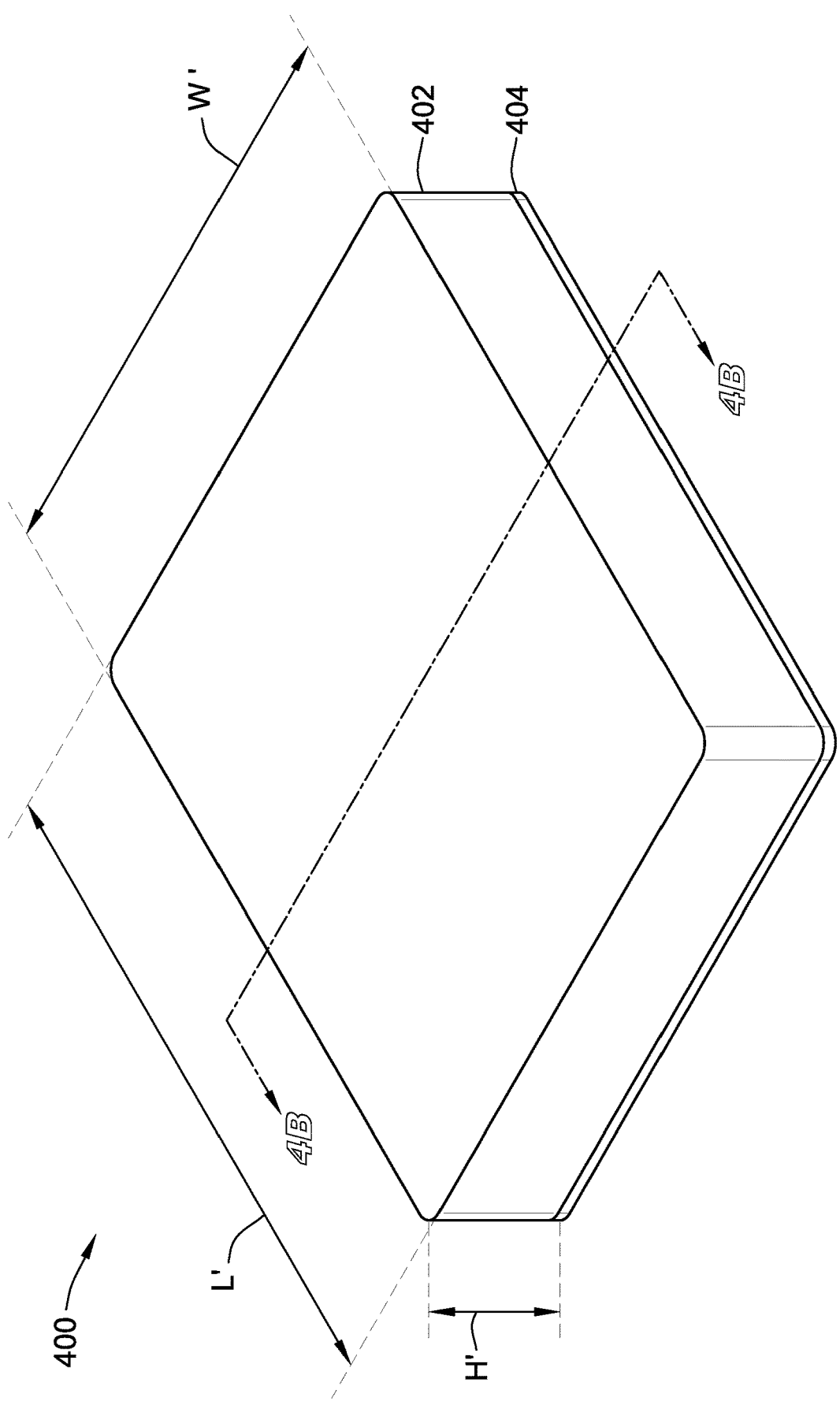
FIG. 4A shows a perspective view of another heat flux device, in accord with aspects of the present concepts.

FIG. 4A shows a perspective view of the alternative heat flux device 400, in accord with aspects of the invention. Similar to the heat flux device 100, the heat flux device 400 can be attached to a location on a user, such as attached to the user's skin, and can be used in determining the core body temperature $T_c$ of the user.

Although shown as a generally rectangular box, the heat flux device 400 can come in various shapes and sizes. For example, the heat flux device 400 can be circular, triangular, hexagonal, oval, etc. According to some embodiments, the shape of the heat flux device 400 corresponds to a specific location for which the heat flux device 400 is configured to attach to the skin. By way of example, and without limitation, the heat flux device 400 can have a butterfly shape for adhering to the user at curved locations, such as on the user's thigh, forehead, etc.

Similar to the heat flux device 100, according to some embodiments, the heat flux device 400 is generally flat and has the shape of a patch. According to such a shape, and according to some embodiments, the heat flux device 400 has a length L' of 2 to 6 mm, such as 4 mm, a width W' of 2 to 6 mm, such as 4 mm, and a height H' of 0.025 to 2 mm, such as 0.3 mm. According to some embodiments, the heat flux device 400 can have other dimensions than the specific dimensions provided herein without departing from the spirit and scope of the present disclosure.

The heat flux device 400 includes an insulation layer 402 above an adhesive layer 404. The insulation layer 402 can be formed of any type of biocompatible insulator, such as, for example, thermoplastics, engineering plastics, and foamy plastics. Specific examples of the insulation materials include, for example, neoprene, HDPE, UMWPE, TEFLON®, PEEK), polyimide, and polyurethane. The insulation layer 402 locally insulates the back (or top) side of the heat flux device 400 with the front (or bottom) side of the heat flux device 400 attached to a user so that the temperature on the back side of the heat flux device 400 can be maintained at a specific temperature (e.g., core body temperature $T_c$) without consuming too much power. This specific temperature is either close to the core body temperature in a cold environment or between the core body temperature and the ambient environmental temperature in a hot environment.

The adhesive layer 404 on the bottom of the insulation layer 402 attaches the heat flux device 400 to the user, such as to the user's skin. The adhesive layer 404 is formed of a biocompatible adhesive, such as, for example, hydrogels, hydrocolloids, acrylics and silicone gels, etc.

FIG. 4B shows a cross-sectional view along the line 4B-4B in FIG. 4A, in accord with aspects of the invention. As shown in FIG. 4B, the heat flux device 400 includes a heat flux pump 406 below the insulation layer 402. The heat flux pump 406 is a bi-directional heat flux pump in that the heat flux pump 406 can transfer heat into the user, through the user's skin, or transfer heat out of the user, again through the user's skin. Specifically, the heat flux pump 406 can be configured as a Peltier cooler, which can combine both the sensing of heat flux based on the Seebeck effect and the pumping of heat based on the Peltier effect. Accordingly, the heat flux pump 406 allows for both the sensing of heat flux at the user's skin and for the pumping of heat either into or out of the user's skin based on both the Seebeck effect and the Peltier effect, respectively. The heat flux pump 406 is coplanar with the adhesive layer 404 to be flush against the user's skin to provide an interface for heat flux to travel between the heat flux pump 406 and the user skin. The ability of the heat flux pump 406 to pump heat allows the heat flux pump 406, among other functionalities, to speed up the process of reaching of steady-state between the heat lost or gained between the user, through the user's skin, and the heat flux device 400 and ambient environment through the insulation layer 402. According to some embodiments, the heat flux pump 406 can be, for example, one of the heat flux sensors 200 or 250 discussed above, that is further connected to a current source (discussed below) for the generation of a current to pump heat based on the Peltier effect.

Based on Equations 1-4 discussed above, a current driven through the heat flux pump 406 can be controlled or regulated to generate heat flux to bring the system (e.g., heat flux device 400 and user's skin) to a steady-state, or a quasi-steady-state, heat flux of zero heat flux. The steady-state can be a quasi-steady-state to account for the constant leak of heat out of or into the heat flux device 400 based on the ambient environmental conditions, which may prevent a perfect steady-state condition. Thus, according to some embodiments, the steady-state can be a quasi-steady-state condition that is at 95%, 98%, or 99% of a steady-state of zero heat flux.

In environments in which the ambient temperature is below the core body temperature, heat flows from the user's skin through the heat flux pump 406, towards the insulation layer 402, and slowly leaks into the environment. In environments in which the ambient temperature is above the core body temperature, heat slowly leaks through the insulation layer 402, towards the heat flux pump 406, and into the user's skin. In both cases, the heat flux pump 406 pumps heat in a specific direction to reach a steady-state of zero heat flux during operation.

The heat flux device 400 also includes a temperature sensor 408. The bottom of the temperature sensor 408 is coplanar with the bottoms of the adhesive layer 404 and the heat flux pump 406. The temperature sensor 408 detects the temperature at the user's skin. Once the system is brought into a steady-state of zero heat flux, the temperature measurement of the temperature sensor 408 provides the core body temperature of the user.

FIGS. 4C and 4D show a top view and a bottom view, respectively, of the heat flux device 400, in accord with aspects of the invention. As shown in FIG. 4C, the top surface of the heat flux device 400 includes the insulation layer 402 that is above the heat flux pump 406 and the adhesive layer 404, which locally insulates the user's skin above the heat flux device 400. As shown in FIG. 4D, the bottom surface of the heat flux device 400 includes the bottom surfaces of the adhesive layer 404, the heat flux pump 406, and the temperature sensor 408.

Figure 4E:
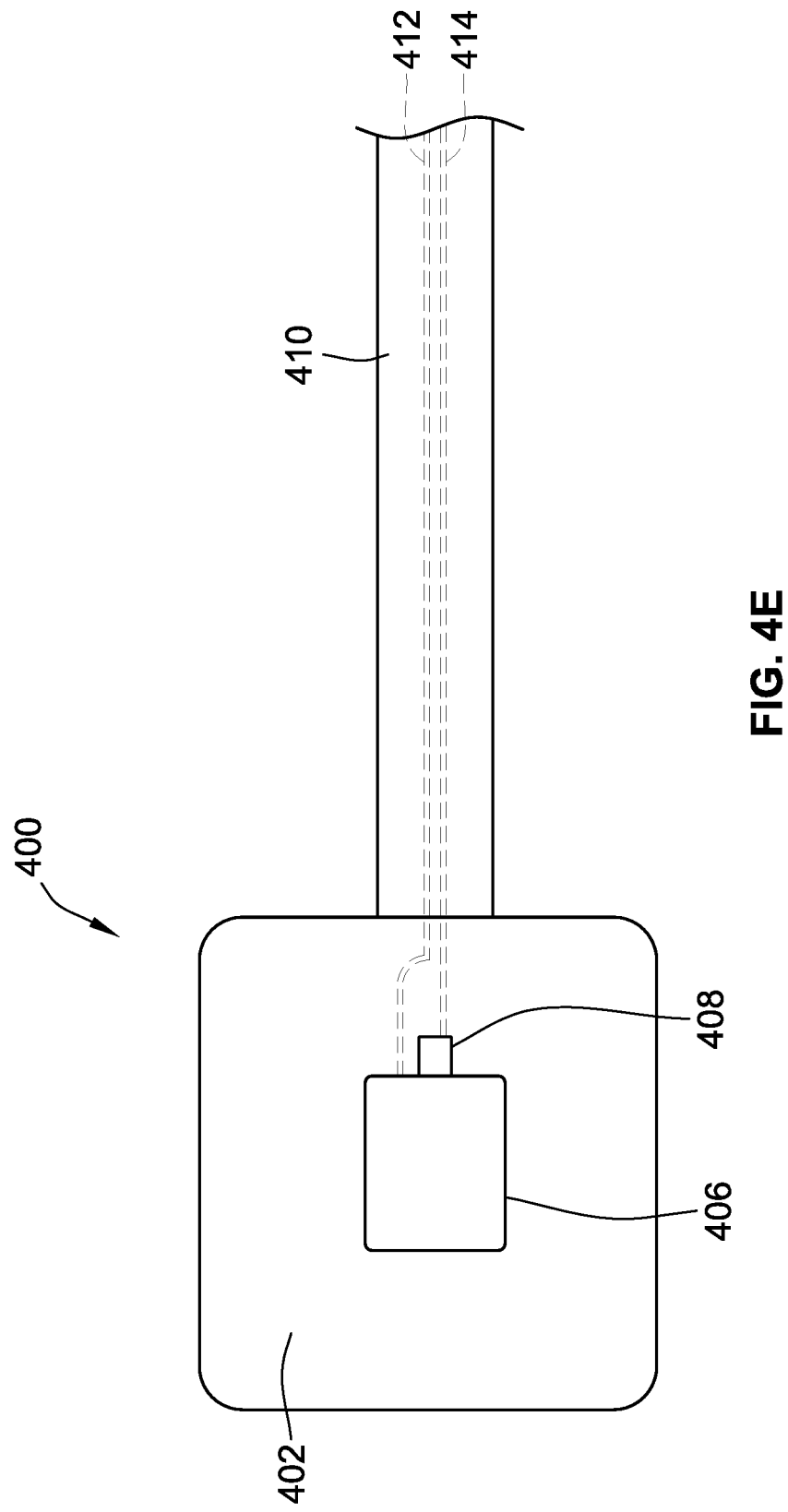
FIG. 4E shows another bottom view of the heat flux device of FIG. 4A with a cable extending from the heat flux device for connecting to other components used in determining the core body temperature, in accord with aspects of the present concepts.

FIG. 4E shows an additional bottom view of the heat flux device 400, including a cable 410, in accord with aspects of the invention. Specifically, the cable 410 extends from one side of the heat flux device 400. The cable 410 includes one or more electrodes that electrically connect to the heat flux pump 406 and the temperature sensor 408. By way of example, and without limitation, the cable 410 can include an electrode 412 that electrically connects to the heat flux pump 406 and an electrode 414 that electrically connects to the temperature sensor 408. Although not shown, opposite ends of the electrodes 412 and 414 can connect to, for example, a logic unit (e.g., controller, processor, etc.) that receives signals from the heat flux device 400 for determining the core body temperature of the user based on the steady-state of zero heat flux and the associated skin temperature at the steady-state, and to a current source for powering the heat flux pump 406 during the transfer of heat, as discussed below.

Although not shown or described above, the heat flux device 100 can include a similar cable as the cable 410, to connect components of the heat flux device 100 (e.g., the heat flux sensor 108 and the temperature sensor 112) to a logic unit (e.g., controller, processor, etc.), storage device, and/or communication components (e.g., transmitter, receiver, transceiver, etc.).

Alternatively, the heat flux device 400 (and the heat flux device 100) may not include the cable 410. Rather, the heat flux device 400 can be entirely self-contained such that, for example, the heat flux device 400 includes a controller, a current source, and a wireless or wired communication component (e.g., transmitter, receiver, transceiver, etc.). Alternatively, the heat flux device 400 can include one or more storage components that allow the heat flux device 400 to store the heat flux measurements and/or temperature measurements. By way of example, and without limitation, the one or more storage components can include flash memory, SRAMs, DRAMs, and the like. Subsequently, the heat flux measurements and/or temperature measurements stored on the one or more storage components can be transferred to an external device for subsequent analysis, storage, and/or display, such as through the cable 410.

According to some embodiments, and similar to the heat flux device 100, the heat flux pump 406 can be encapsulated to protect the heat flux pump 406 from corrosion, such as sweat-induced corrosion. Moreover, the material used to encapsulate the heat flux pump 406 can have a low thermal resistivity that allows the heat flux pump 406 to detect changes in temperature. Further, other portions of the heat flux device 400 can be formed of materials that are resistant to corrosion, or also can be encapsulated to protect these portions. Alternatively, the entire heat flux device 400 can be encapsulated within an encapsulation material to protect the heat flux device 400 from corrosion.

Referring to FIG. 5, FIG. 5 shows operation of the heat flux device 400 attached to the skin 500 of a user, in accord with aspects of the invention. With the heat flux device 400 attached to the skin 500 of a user, the heat flux device 400, through the heat flux pump 406, measures the heat flux out of the skin 500. Specifically, arrows 502 generally represent the heat flux generated from the user that is transferred to the heat flux pump 406 based on conduction, convention, and/or radiation.

Prior to the heat flux device 400 registering a steady-state of zero heat flux while attached to the user, the heat flux device 400 either pumps heat into the user or draws heat away from the user based on the Peltier effect. Arrows 504 represent heat being pumped into the user or drawn from the user based on current flowing through the heat flux pump 406. Based on the ability of the heat flux pump 406 to pump heat into or out of the user through the user's skin, the heat flux device 400 can be used in both cold and warm environments, where previously wearable sensors based on the ZHF technique were limited to only cooler environments where the ambient temperature was less than the typical core body temperature. Once the heat flux device 400 registers a steady-state, or a quasi-steady-state, of zero heat flux, the temperature sensor 408 measures the temperature at the skin 502, which corresponds to the core body temperature $T_c$.

Figure 6:
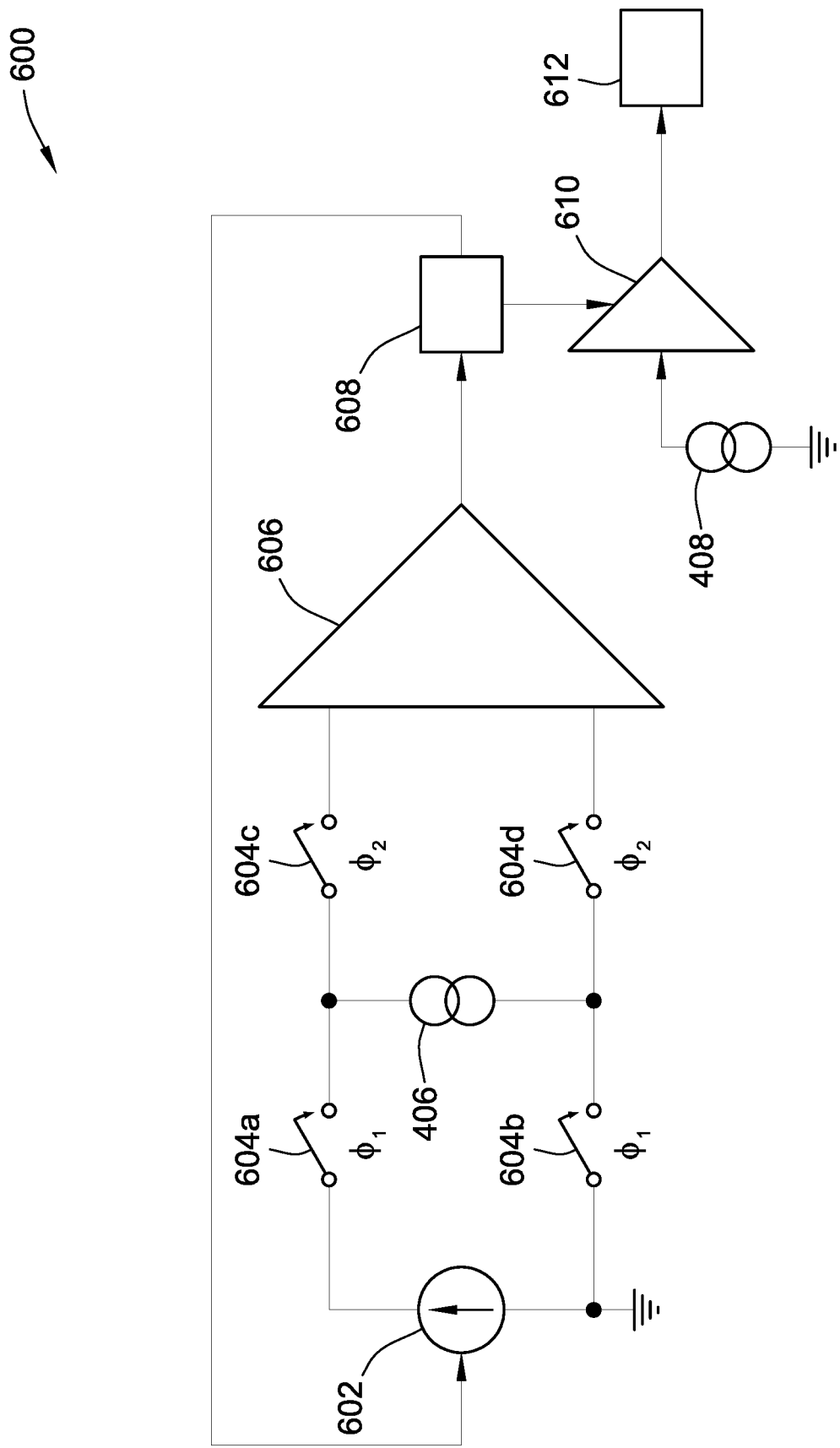
FIG. 6 shows a circuit diagram of a circuit for controlling the heat flux device of FIG. 4A, in accord with aspects of the present concepts.

FIG. 6 shows a circuit diagram of a circuit 600 associated with the above-described operation of the heat flux device 400, in accord with aspects of the present disclosure. The circuit 600 includes the heat flux pump 406 and the temperature sensor 408. Although shown as two separate components within the circuit 600, as described above, the heat flux pump 406 and the temperature sensor 408 can be both part of the heat flux device 400.

The circuit 600 includes a current source 602 (e.g., a battery) to deliver current to the heat flux pump 406 for transferring heat. The current source 602 may be any type of current source for an electronic device, such as, but not limited to, one or more electrochemical cells or batteries, one or more photovoltaic cells, one or more piezoelectric elements, or a combination thereof. The one or more electrochemical cells or batteries may be rechargeable or non-rechargeable. In the case of the photovoltaic cells, the cells may charge one or more electrochemical cells and/or batteries. According to some embodiments, the current source 602 can be located on and/or within the heat flux device 400 or, alternatively, can be located remotely from the heat flux device 400, such as connected to the heat flux device 400 through the cable 410.

The circuit 600 also includes switches 604a-604d and a recording circuit 606. During the transfer of heat, also referred to a Phase 1 ($\phi_1$), switches 604a and 604b are closed and switches 604c and 604d are open to direct the flow of current from the current source 602 to the heat flux pump 406. During the sensing of heat flux, also referred to a Phase 2 ($\phi_2$), switches 604a and 604b are open and switches 604c and 604d are closed to direct the flow of current generated by the heat flux pump 406 based on the Seebeck effect and any temperature differential between the top and bottom of the heat flux pump 406 to a recording circuit 606. According to one embodiment, the recording circuit 606 records a 1 or a 0 depending on whether the heat flux pump 406 senses heat flux or senses no heat flux (e.g., no appreciable heat flux registered by the heat flux pump 406, or below some threshold value). Alternatively, the recording circuit 606 records a specific value for the detected heat flux, such as a specific voltage generated by the heat flux pump 406.

The circuit 600 further includes a logic unit 608 that determines, from information generated by the recording circuit 606, if the heat flux at the heat flux pump 406 is zero (or within some threshold value (or values) that is effectively zero) to determine if the heat flux is at a steady-state (or a quasi-steady state). If the heat flux is not at a steady-state (or quasi-steady state) of zero heat flux (or within some threshold value (or values) that is effectively zero), the logic unit 608 then controls the application of current from the current source 602 to the heat flux pump 406 until the heat flux measured by the heat flux pump 406 is zero. According to some embodiments, the logic unit 608 determines a direction of the current through the heat flux pump 406 to determine whether to transfer heat into the skin or to transfer heat out of the skin, depending on the current heat flux and the heat flux required to reach the steady-state. Specifically, depending on the direction of the current through the heat flux pump 406, n/p-conductor junctions within the heat flux pump 406 selectively heat one side of the heat flux pump 406 and cool the other side of the heat flux pump 406 to transfer heat out of or into the user's skin depending on the state of the heat flux.

Once the heat flux at the heat flux pump 406 is at a steady-state of zero heat flux, the logic unit 608 enables a recording circuit 610. The recording circuit 610 acquires, from the temperature sensor 408, the temperature at the surface of the skin of the user. Because the heat flux at the surface of the user's skin is at a steady-state of zero heat flux, the temperature measured by the temperature sensor 408 is the core body temperature $T_c$. Thus, the skin temperature is passed to a logic unit 612. The logic unit 612 determines the core body temperature of the user based on the skin temperature when the heat flux is zero.

Although shown as four separate units, according to some embodiments, the recording circuit 606, the logic unit 608, the recording circuit 610, and the logic unit 612 can be combined into the same unit or component, such as a single logic unit or controller. According to some embodiments, information generated by the heat flux device 400, such as from the heat flux pump 406 and the temperature sensor 408, is fed into a proportional-integral-derivative (PID) controller, which can be analog or digital, to control the heat flux device 400 as described above in FIG. 6 for determining the core body temperature. Accordingly, one or more of the recording circuit 606, the logic unit 608, the recording circuit 610, and the logic unit 612 can be embodied in the form of the PID controller.

Although not shown for illustrative convenience, the circuit 600 can include ancillary circuitry for the circuit 600 to operate as described above. By way of example, the circuit 600 can include ancillary circuitry to control the supply of current from the current source 602. Additionally, the circuit 600 can include ancillary circuitry to control the operation of the switches 604a-604d. Thus, the circuit 600 can include circuitry in addition to what is described herein without departing from the spirit and scope of the present disclosure.

According to some embodiments, to reduce the load on the current source 602 in reaching a steady-state for the heat flux of the system (e.g., user's skin and heat flux device 400), the heat flux device 400 can be heated to approximately the core body temperature, such as 37° C. Preheating the heat flux device 400 prior to placing the heat flux device 400 on the user minimizes the consumption of current for thermal balancing to reach the steady-state of zero heat flux.

Based on the foregoing, the heat flux device 400 can be worn by a user to determine the core body temperature of the user in both warm environments (warmer than typical core body temperatures) and cold environments (colder than typical core body temperatures). As described above, the heat flux device 100 can be worn by a user at locations prone to sweating, while including a determination of the evaporative cooling of the sweat in the determination heat flux. According to some embodiments, only one of the above-described heat flux devices 100 and 400 is worn by the user to determine the core body temperature. Alternatively, both of the heat flux devices 100 and 400 can be worn by the user to determine the core body temperature. Both of the heat flux devices 100 and 400 can be worn in generally the same location to determine an averaged core body temperature for the location. In such an embodiment, the heat flux devices 100 and 400 can be combined into a single device that includes both of the heat flux devices 100 and 400. Alternatively, the heat flux devices 100 and 400 can be worn at separate locations on the body to determine an averaged core body temperature that compensates for potential variations in core body temperature based on location at which the core body temperature is measured.

Figure 7:
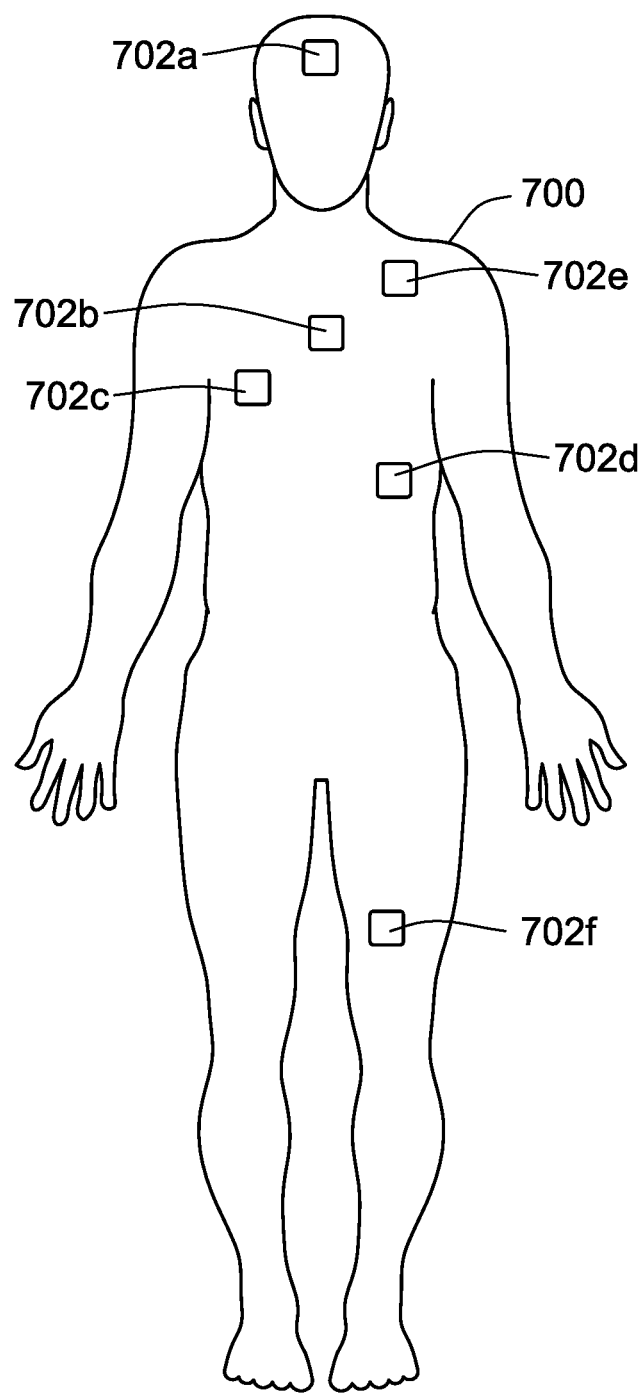
FIG. 7 illustrates exemplary locations of the heat flux devices of FIGS. 1A and 4A on a user, in accord with aspects of the present concepts.

FIG. 7 illustrates exemplary locations of the heat flux devices 100 and 400 on a user 700, in accord with aspects of the invention. Specifically, FIG. 7 shows locations 702a-702f of the heat flux sensors 100 and 400 on the user 700. The locations 702a-702f represent locations on the body that are suitable for heat flux measurements and core body temperature measurements. The locations include, for example, the forehead 702a, the sternum 702b, the pectoralis 702c, the rib cage 702d, the scapula 702e, and the thigh 702f. In addition to the locations illustrated in FIG. 7, and according to some embodiments, the heat flux devices 100 and 400 can be mounted on or above major arteries and veins to observe thermoregulation of the body.

The above-described heat flux devices and associated methods for determining the core body temperature have applications in, for example, heat strain detection (e.g., hypothermia and hyperthermia), thermoregulation monitoring for chronic disease patients (e.g., patient's suffering from diabetes, hyperthyroidism, and hypothyroidism), fever detection, surgical room patient monitoring, human performance measuring (e.g., thermal output), sports training, and thermal design of garments, among other various uses not specifically mentioned herein.

While particular embodiments and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of the invention as defined in the appended claims.

What is claimed is:

1. A heat flux device wearable at a location on a user, the heat flux device comprising:
   a heat flux sensor configured to be in contact with the user and detect heat flux at the location, the heat flux sensor comprising a plurality of thermocouple junctions; and
   a wicking layer having a bottom surface configured to be in contact with the user and a top surface configured to be exposed to an environment of the user, the wicking layer including a first portion and a second portion, the first portion surrounding at least part of vertical sides of the heat flux sensor and the second portion covering a top surface of the heat flux sensor, the wicking layer configured to absorb moisture at the location through the first portion and to transport the moisture to the second portion for evaporation above the heat flux sensor, wherein the heat flux detected by the heat flux sensor includes evaporative cooling from the evaporation of the moisture.

2. The heat flux device of claim 1, wherein the heat flux sensor includes a thermal resistance layer, and the heat flux sensor is configured to detect the heat flux based on a temperature differential across the thermal resistance layer.

3. The heat flux device of claim 2, wherein the heat flux sensor includes a first thermocouple junction that detects a first temperature on a first side of the thermal resistance layer and a second thermocouple junction that detects a second temperature on a second side of the thermal resistance layer, opposite the first side, and the temperature differential is based on a difference between the first temperature and the second temperature.

4. The heat flux device of claim 2, wherein the temperature differential generates a voltage based on the Seebeck effect, and the heat flux is determined based on the voltage.

5. The heat flux device of claim 1, wherein a bottom surface of the heat flux sensor and the bottom surface of the first portion of the wicking layer are substantially equal in surface area.

6. The heat flux device of claim 1, further comprising:
an adhesive layer covering a bottom surface of the first portion of the wicking layer,
wherein the adhesive layer is at least partially perforated.

7. The heat flux device of claim 6, wherein a bottom surface of the adhesive layer and a bottom surface of the heat flux sensor are substantially coplanar.

8. The heat flux device of claim 1, further comprising an insulation layer above the first portion of the wicking layer and surrounding the second portion of the wicking layer.

9. The heat flux device of claim 8, wherein a top surface of the insulation layer and a top surface of the second portion of the wicking layer are substantially coplanar.

10. The heat flux device of claim 1, further comprising:
a temperature sensor configured to determine a skin temperature of the user at the location.

11. The heat flux device of claim 10, wherein a bottom surface of the temperature sensor is substantially coplanar with a bottom surface of the heat flux sensor.

12. The heat flux device of claim 1, wherein the first portion and the second portion of the wicking layer at least partially overlap at an overlap area, and the overlap area is configured to transport fluid from the first portion to the second portion.

13. The heat flux device of claim 12, wherein the fluid is transported based on a capillary action.

14. The heat flux device of claim 12, wherein the first portion of the wicking layer is formed of a moisture-absorbing material.

15. The heat flux device of claim 12, wherein the second portion of the wicking layer is formed of a skin-simulating material.

16. A method of determining heat flux using a heat flux sensor at a location on a user, the method comprising:
absorbing moisture from the location on the user through a bottom region of a heat flux device placed at the location and in contact with the user;
transporting the moisture to a top region of the heat flux device above the heat flux sensor within the heat flux device, the heat flux sensor comprising a plurality of thermocouple junctions; and
determining the heat flux at the location on the user by the heat flux sensor, the heat flux including the evaporative heat flux resulting from evaporation of the moisture at the top region,
wherein the moisture is absorbed through a first portion of a wicking layer in contact with the user at the bottom region of the heat flux device and is transported to a second portion of the wicking layer at the top region of the heat flux device and exposed to an environment of the user.

17. The method of claim 16, further comprising:
measuring a first temperature at the bottom region of the heat flux device; and
measuring a second temperature at the top region of the heat flux device,
wherein the evaporative heat flux is determined based, at least in part, on a difference between the first temperature and the second temperature.

18. The method of claim 16, wherein the location is on skin of the user at a forehead, a sternum, a pectoralis muscle, a rib cage, a scapula, or a thigh.

19. The method of claim 16, wherein a surface area of the bottom region of the heat flux device through which the moisture is absorbed is substantially equal to a surface area of a bottom surface of the heat flux sensor.

20. The method of claim 16, wherein the first portion of the wicking layer is formed of a moisture-absorbing material.

21. The method of claim 16, wherein the second portion of the wicking layer is formed of a skin-simulating material.

22. The method of claim 16, further comprising:
attaching the heat flux device on the location of the user based on an adhesive layer surrounding the heat flux sensor on a bottom surface of the heat flux device.

23. The method of claim 22, wherein the adhesive layer is at least partially perforated.

* * * * *